(12) United States Patent
Lindquist et al.

(10) Patent No.: US 8,332,235 B2
(45) Date of Patent: *Dec. 11, 2012

(54) METHOD AND COMPUTER PROGRAM PRODUCT FOR MEASURING AND UTILIZING EFFICIENCY OF MEDICAL RESOURCE AND SERVICES PROVIDERS

(75) Inventors: Tammie J. Lindquist, Plymouth, MN (US); Robert P. Power, St. Paul, MN (US); Gary J. Kitching, Prescott, WI (US); Susan L. Cooper, Eagan, MN (US); Chad C. Heim, Farmington, MN (US); Richard R. Paskach, Eagan, MN (US)

(73) Assignee: Group Health Plan, Inc., Bloomington, MN (US)

( * ) Notice: Subject to any disclaimer, the term of this patent is extended or adjusted under 35 U.S.C. 154(b) by 432 days.

This patent is subject to a terminal disclaimer.

(21) Appl. No.: 12/684,421

(22) Filed: Jan. 8, 2010

(65) Prior Publication Data

US 2010/0114611 A1    May 6, 2010

Related U.S. Application Data

(63) Continuation of application No. 11/303,615, filed on Dec. 16, 2005, now Pat. No. 7,831,443.

(51) Int. Cl.
| | |
|---|---|
| *G06Q 10/00* | (2006.01) |
| *G06Q 50/00* | (2006.01) |
| *A61B 5/00* | (2006.01) |
| *G06F 19/00* | (2006.01) |

(52) U.S. Cl. ............................................. 705/2; 705/3
(58) Field of Classification Search .................. 705/2–3
See application file for complete search history.

(56) References Cited

U.S. PATENT DOCUMENTS 5,018,067 A * 5/1991 Mohlenbrock et al. ........ 600/300
5,652,842 A * 7/1997 Siegrist et al. ..................... 705/2

(Continued)

OTHER PUBLICATIONS

Bridges to Excellence, "Measuring Provider Efficiency Version 1.0", Dec. 31, 2004 (51 pages).
Symmetry, "Episode Treatment Groups, An Illness Classification and Episode Building System", May 20, 2005 (16 pages).

(Continued)

*Primary Examiner* — Robert Morgan
*Assistant Examiner* — Joy Chng
(74) *Attorney, Agent, or Firm* — Winthrop & Weinstine, P.A.

(57) ABSTRACT

A method and computer program product is provided that, in various embodiments, may provide a measure of efficiency of resources used in medical treatment plan options. A normalized Relative Resource Value (RRV) may be obtained that measures the level of resources required to satisfy a "normal" case for a particular aspect of medical care. Applying this value against actual costs allows ranking and/or comparison of health care providers relative to one another on the basis of the price or resources applied or utilized. Moreover, applying the RRV against the quality of outcome allows comparison and ranking of providers on overall value. The invention may be applied to the components of medical care comprising, inter alia, acute inpatient, non-acute inpatient, outpatient, professional office-based care including scheduled outpatient, and pharmacy/prescriptions. The normalized RRV obtained under various embodiments of the invention may measure resource use for medical treatment plan options/resources independent of price. The RRV may be relative across, as well as within, each of the components of medical care. Thus, provider profiling generally as well as profiling across treatment plan options based on efficiency generally is within the scope of various embodiments of the invention. Moreover, providers may be compared based on efficiency for specific conditions, as well as across conditions, across treatment plan options and across components of care using various embodiments of the invention.

11 Claims, 6 Drawing Sheets

U.S. PATENT DOCUMENTS

| | | | |
|---|---|---|---|
| 5,918,208 A | 6/1999 | Javitt | |
| 6,223,164 B1 | 4/2001 | Seare et al. | |
| 2003/0212707 A1* | 11/2003 | Uber et al. | 707/104.1 |
| 2004/0078236 A1* | 4/2004 | Stoodley et al. | 705/2 |
| 2006/0190295 A1* | 8/2006 | Merkin | 705/2 |

OTHER PUBLICATIONS

Edward Bassin, ProSoft, Inc., Cambridge, Massachusetts, "Episodes of Care, A Tool for Measuring the Impact of Healthcare Services on Cost and Quality", May 20, 2005 (7 pages).

* cited by examiner

METHOD AND COMPUTER PROGRAM PRODUCT FOR MEASURING AND UTILIZING EFFICIENCY OF MEDICAL RESOURCE AND SERVICES PROVIDERS

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

RELATED APPLICATION(S)

None.

FIELD OF THE INVENTION

This invention relates generally to measuring, ranking and/or comparing efficiency of the provision of medical resources and services.

BACKGROUND OF THE PRESENT INVENTION

One of many major challenges facing risk-bearing payer organizations in today's managed healthcare environment is to find a way to accurately measure resource use for medical procedures/treatment plan options and services independent of pricing. Such a measurement may create a relative value scale that is independent of price and that crosses inpatient, outpatient, professional office-based care and prescription drugs. This relative value scale may then, in turn, be used to compare and contrast various services and providers.

Developing a scale that is independent of price is relatively difficult. Some reasons for this difficulty include provider payments dramatically differing in price. Provider payments may often be applied at a case rate, not connected to the discrete services. Utilization patterns also vary dramatically between providers. Thus, utilization is difficult to distinguish from price and place of the actual drivers for service cost.

The Center for Medicare and Medicaid Services (CMS) has developed three sets of relative weighting systems for different aspects of medical care. The first system, "Diagnosis-Related Groups" (DRGs), are a classification of hospital case types into groups expected to have similar hospital resource use. Medicare uses this classification to pay for inpatient hospital care. The groupings are based on diagnoses, treatment plan options, age, sex, and the presence of complications or comorbidities. DRG's apply primarily to acute inpatient care.

The second weighting system is known as Outpatient Prospective Payment System (OPPS) and utilizes "Ambulatory Payment Classifications" (APC). The OPPS system deals primarily with outpatient care. The OPPS essentially transfers some financial risk for outpatient services from Medicare to hospitals and to give hospitals incentives to be more efficient. Additionally, the OPPS was designed to reduce Medicare beneficiary co-payments from 20% of Medicare billed charges to 20% of the Medicare allowable charges. Usage of the OPPS fundamentally changed Medicare's reimbursement for hospital outpatient services from a cost basis (unique to each hospital) to a standardized prospective payment, similar to the fixed payments for items on the physician fee schedule. Every outpatient service does not have its own APC. The designated APC for a service is the method Medicare uses to determine reimbursement.

The third CMS weighting system provides a standardized physician payment schedule using a "Resource-Based Relative Value Scale (RBRVS) for professional office-based care. Under the RBRVS system, payments for services are determined by the resource costs needed to provide them. The cost of providing each service is divided into three components: physician work, practice expense and professional liability insurance. Payments are calculated by multiplying the combined costs of a service by a conversion factor. The RBRVS conversion factor is a monetary amount that is determined by CMS.

The currently available CMS weighting scales each focus on particular components of medical care: DRG focuses on acute inpatient care; APC is directed to outpatient care; and RBRVS focuses on professional office-based care. The CMS scales apply the types of services covered by Medicare and, as a result, certain services such as non-acute inpatient and pharmacy services are excluded. In addition, the APC scale, e.g., groups many services that are deemed to have comparable resource utilization, whether that is actually the case or not. DRG, RBRVS and APC each use differing scales or units of measure, thus simply combining efficiency measures across each of the relative weighting scales would be inappropriate and may be misleading.

It would be desirable to have a medical care efficiency measure that includes services not covered by the CMS weighting scales. In addition, it would be desirable for such an efficiency measure to allow comparison within a particular medical condition as well as across all conditions, both within and across providers. Among other things, such a comparison may be very useful to individual patient, particularly in light of Health Savings Accounts and increasing member liability and deductibles. Such benefit plans place some of the risks and rewards of selecting a medical provider in the hands of the individual patient as a medical resource consumer.

SUMMARY OF THE INVENTION

A method and computer program product is provided that, in various embodiments, may provide a measure of efficiency of resources used in medical treatment plan options. A normalized Relative Resource Value (RRV) may be obtained that measures the level of resources required to satisfy a "normal" case for a particular aspect of medical care. Applying this value against actual costs allows ranking and/or comparison of health care providers relative to one another on the basis of the price or resources applied or utilized. Moreover, applying the RRV against the quality of outcome allows comparison and ranking of providers on overall value. The invention may be applied to the components of medical care comprising, inter alia, acute inpatient, non-acute inpatient, outpatient, professional office-based care including scheduled outpatient, and pharmacy/prescriptions. The normalized RRV obtained under various embodiments of the invention may measure resource use for medical treatment plan options/resources independent of price. The RRV may be relative across, as well as within, each of the components of medical care. Thus, provider profiling generally as well as profiling across treatment plan options based on efficiency generally is within the scope of various embodiments of the invention. Moreover, providers may be compared based on efficiency for specific conditions, as well as across conditions, across treatment plan options and across components of care using various embodiments of the invention.

An object of the present invention is to provide a method, system and computer program product for developing a relative value scale comprising inpatient, outpatient, professional office-based care, and prescription drug data.

Another object of the present invention is to provide a method, system and computer program product for developing a relative value scale comprising acute inpatient and non-acute inpatient, outpatient, professional office-based care, and prescription drug data.

Another object of the present invention is to provide a method, system and computer program product for developing a value that may be used to measure resource use for treatment plans, and comparison of providers by treatment plan options, that is independent of price.

Still another object of the present invention is to provide a method, system and computer program product for developing a value that may be used to measure resource use for medical treatment plan options that crosses acute inpatient, non-acute inpatient, outpatient, professional office-based care and prescription drug data.

Another object of the present invention is to provide operations management tools for the health care provider by generating key operational metric data for analysis.

Yet another object of the present invention is to enable the building and management of an efficient health care provider network.

Another object of the present invention is to facilitate the improvement of health care by evaluating and comparing the resources applied against the resulting outcome.

Another object of the present invention is to facilitate the identification of misuse of health care resources.

Still another object of the present invention is to measure relative price for treatment plans across various conditions and providers, allowing for collaborative combination and implementation.

Another object of the present invention is to provide a measure that allows for the efficient use of drug care.

Still another object of the present invention is to provide a method that may be combined with, inter alia, episodes of care or other treatment or patient grouper methodology.

Yet another object of the present invention is to provide a method of determining relative value for new treatment plans and/or options.

Another object of the present invention is to provide a measurement of efficiency that does not penalize health care providers that provide more complete care.

The foregoing objects of various embodiments of the invention will become apparent to those skilled in the art when the following detailed description of the invention is read in conjunction with the accompanying drawings and claims. Throughout the drawings, like numerals refer to similar or identical parts.

The figures and the detailed description that follow more particularly exemplify these and other embodiments of the invention

DETAILED DESCRIPTION OF THE INVENTION

With reference to the accompanying Figures, there is provided a method, system and computer program product for measuring efficiency of the provision of health care.

The following definitions apply throughout this document.

Efficiency: A determination of the comparative medical claim resources used to treat similar conditions or sets of conditions and ignores the impact of price variation between providers by constructing a universal fee schedule via cost normalization. The case mix adjustment may be applied to aggregate across patients with different sets of conditions.

Cost Normalization: The act of applying a standard fee schedule to all providers, regardless of existing charge structures and health plan contract arrangements.

Rate: Dollars per unit.

Episode of Care: An episode of care is a series of billed charges from a hospital, doctor or health care provider that represents all of the care received during a physician visit, surgery or inpatient hospital stay. An episode of care is typically made up of charges for many individual services. Total billed charges related to an episode of care can vary based on the different individual services received during an episode of care.

Example

If one patient is admitted to the hospital for pneumonia and has a chest X-ray while a second patient is also admitted to the hospital for pneumonia, but does not have a chest X-ray, the total billed charges for each member will be different for a similar episode of care.

Figure 1:
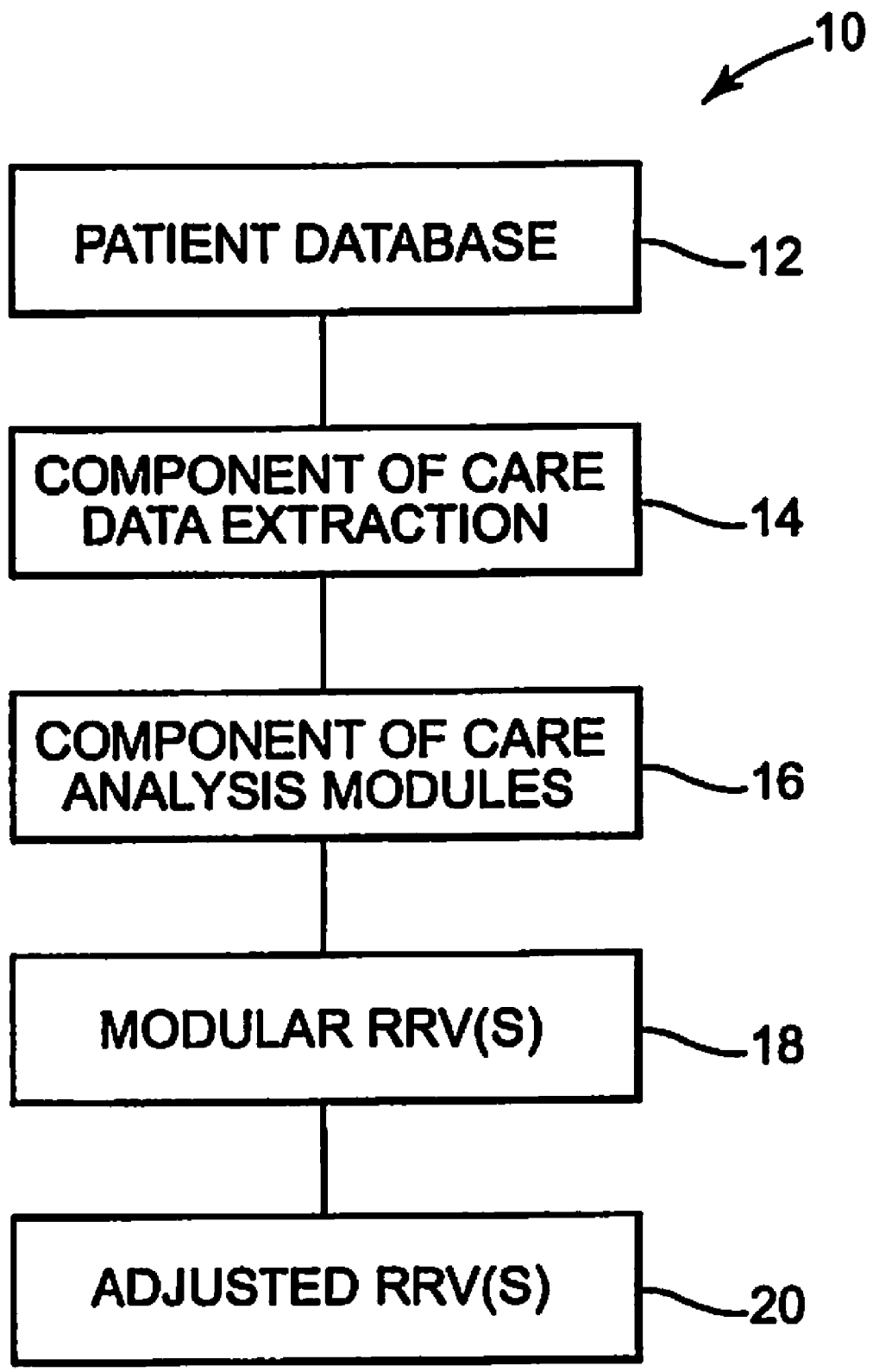
FIG. 1 is a flowchart providing an overview of a preferred embodiment of the inventive method.

Referring now to FIG. 1, in a broad sense, embodiments of the invention may provide a method, system and computer program product that extracts data relating to at least one component of care, e.g., acute inpatient, non-acute inpatient, outpatient, professional office-based care, and prescriptions, from an existing patient database. Thus, the relative resource valuation method 10 may comprise a patient database 12 from which data specific to a particular component of care may be extracted 14. The extracted data may be provided to the appropriate component of care module 16, e.g., an acute inpatient module, a non-acute inpatient module, an outpatient module, a professional office-based care module and a prescription module may be provided. Other modules comprising additional components of care may present themselves to those skilled in the art, moreover, the components of care in the illustrated modules may be broken into sub-components by those skilled in the art. Each possibility is within the scope of the inventive process. As will be described in detail infra, each module comprises methodology, e.g., computer code, to determine the resource use in performance of the respective treatment plan option or service. The billed amount is used as the payment basis in the initial calculations and all available weights, DRG, APC and RBRVS, are utilized where applicable to determine resource use. In general, where a weight scale does not exist for a particular treatment plan option, item or service, an average billed amount or other surrogate weight may be used. Each module develops an overall rate using the billed amounts and the appropriate weights for each weight scale. This rate may be applied back to the data to obtain the modular normalized Relative Resource Value (RRV) 18. Ultimately, to create relativity and thus comparability of RRVs between modules, the modular RRVs may be adjusted to obtain adjusted RRVs 20. Such adjustment may be accomplished by calculation of the ratio between the amount billed and the amount paid. Application of this billed/paid ratio to the modular RRVs allows inter-modular comparison of the adjusted RRVs.

Additional uses of the invention include developing a relative value scale comprising inpatient (acute or non-acute), outpatient, professional office-based care, and prescription drug data and wherein the obtained value may be used to measure resource use for treatment plans, and comparison of providers by treatment plan options, that is independent of price.

Further, the relative value obtained using the invention may be used to measure resource use for medical treatment plan options that crosses acute inpatient, non-acute inpatient, outpatient, professional office-based care and prescription drug data.

Operations management may use the inventive method as a tool for the health care provider by generating key operational metric data for analysis.

The invention may enable the building and management of an efficient health care provider network and/or to facilitate the improvement of health care by evaluating and comparing the resources applied against the resulting outcome as well as facilitation of the identification of misuse of health care resources.

The invention described herein may further be used to measure relative price for treatment plans across various conditions and providers, allowing for collaborative combination and implementation and/or to provide a measure that allows for the efficient use of drug care.

The invention may further provide a method that may be combined with, inter alia, episodes of care or other treatment or patient grouper methodology and/or to provide a method of determining relative value for new treatment plans and/or options.

Finally, the invention described herein may provide a measurement of efficiency that does not penalize health care providers that provide more complete care, so that preventive care is not undervalued.

Figure 2:
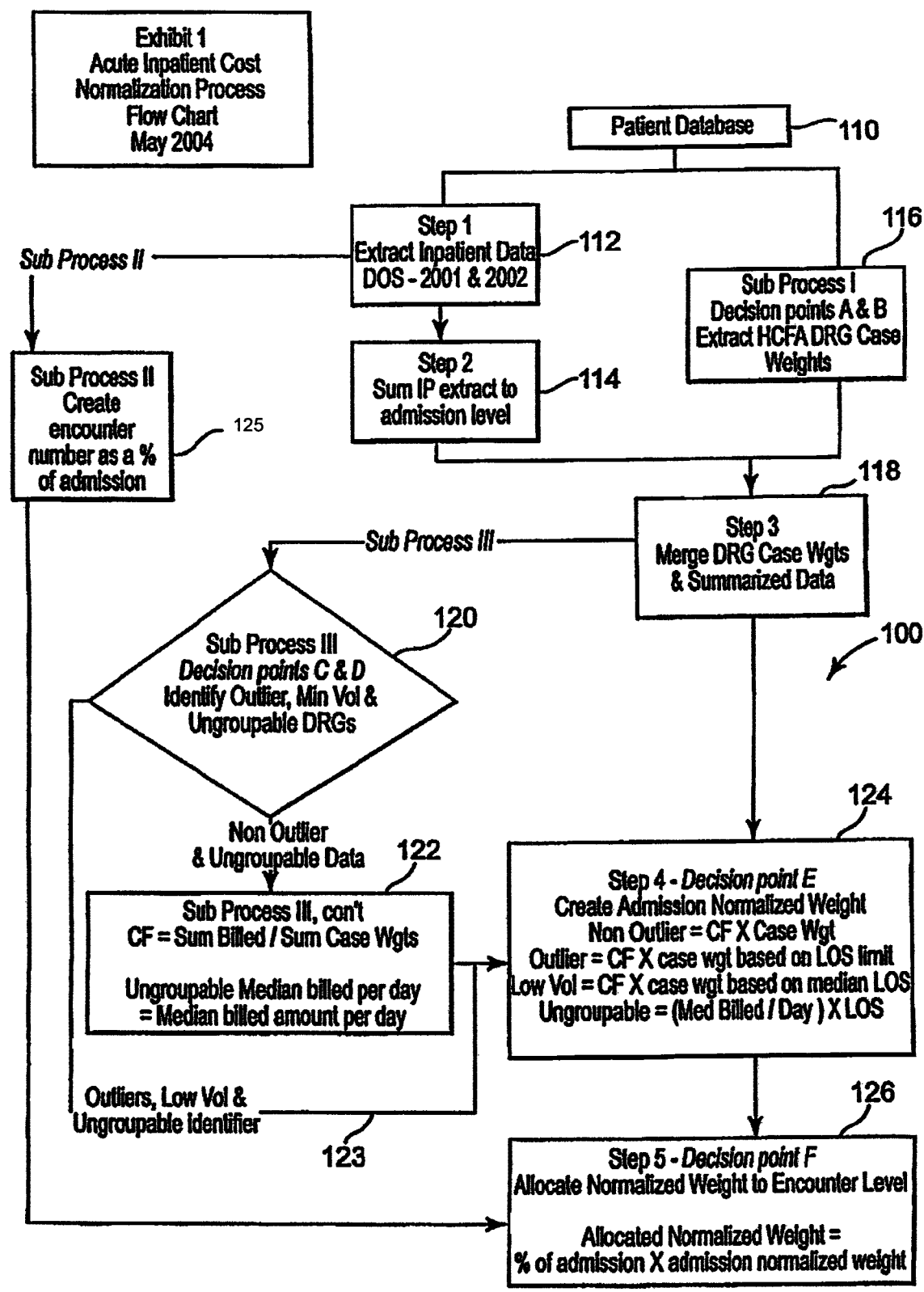
FIG. 2 is a flowchart illustrating a preferred embodiment for the acute inpatient module of the inventive method.

FIG. 2 provides a process flow for an embodiment of the inventive efficiency measurement for the acute inpatient component of medical care module 100. The normalized value or RRV developed with this particular process measures efficiency of resource use for a "normal" inpatient service. The RRV may be relative within and across services comprising the inpatient care environment as well as to the other components of care: non-acute inpatient; outpatient; professional office-based care; and pharmacy.

Where available, current CMS weighting systems are used in the invention to determine the resource use for a specific treatment plan option or care episode, but additional normalization processes may be applied to create the desired relativity. In the case of acute inpatient, the DRG-based weight scale is available and will be utilized. The billed amount will be used to create relativity, and thus comparability, of the acute inpatient RRV with the remaining components of care described above. The billed amount, as opposed to the paid amount, is used in various embodiments of the invention because it is most representative of resource use at the line item level. For example, the billed amount is unaffected by contract rates, payment discounts or payment methodologies. The paid or contracted fee amount may be used in alternate embodiments, subject to these qualifying limitations.

Returning now to FIG. 2, a database of patient data is provided 110. Acute inpatient data is extracted 112 from the database and organized by encounter. Next, the extracted data may be summed to an admission level 114. This summation ensures that all medical care encounters occurring within a single patient admission are evaluated. In the preferred embodiment, admissions with a billed amount of zero ($0) are deleted, as are those admissions with negative billed amounts.

The DRG case weights are then extracted 116 from the patient database 110 and merged with the inpatient data previously summed to admission level 118. At this point, in various embodiments, outliers, low volume admissions and ungroupable DRGs may be identified in preparation for calculation of the conversion factor 120. Each identified data category may be analyzed slightly differently under the inventive process.

Outliers may be identified by use of statistical techniques involving creation of a standard deviation range using length of stay (LOS) data within DRG. Thus, using techniques well known in the art, a range of data is selected for continuing analysis. This data range may have a median and standard deviations (SD) may be calculated, thereby establishing upper and lower data limits. In this manner, outliers may be identified if the data point is outside either the upper or lower limit of the stated standard deviation range. For example, a preferred range may be six SD (+/−3 SD about the median), however, a tighter range may also be used in various embodiments, e.g., 4 SD (+/−2 SD about the median). Similarly, a wider range, e.g., 8 SD (+/−4 SD about the median) may be used. The width of the applicable standard deviation range used to identify outliers is dependent upon the goals for the process as those skilled in the art will readily recognize.

Low volume admissions may be defined as those DRGs having less than a statistically significant number of admissions. In the preferred embodiment, a low volume admission may be defined as DRGs with less than five (5) admissions. Again, depending upon the goal for the overall process and the importance of robustness of results, the low volume threshold may either increase, e.g., require less than 10 admissions within a DRG to qualify as low volume admissions, or decrease, e.g., requiring less than 3 or 2 admissions. As described above, the preferred embodiment utilizes a statistically significant number of admissions as those skilled in the art will recognize.

Ungroupable DRG's may be defined as admissions that are either lacking sufficient information in the patient database or there is an obvious coding error. For example, an admission that is missing procedure codes is an ungroupable DRG for purposes of this invention. Similarly, a coding indicating that a male patient underwent a hysterectomy also qualifies as an ungroupable DRG.

The outliers, low volume admissions and ungroupable DRG data are then flagged within the dataset for further processing.

After identification and flagging of outliers, low volume admissions and ungroupable DRG data is complete, a data conversion factor is developed from the "normal" acute inpatient dataset excluding the data previously identified as either being an outlier, low volume or ungroupable DRG 122. The "normal" conversion factor may be obtained by summing the data to the aggregate level. The conversion factor is then calculated as the sum of the overall billed amount divided by the sum of the DRG case day weights.

The admission level modular RRV's may now be calculated 124, including separate calculations involving the previously identified outlier, low volume admission and ungroupable DRG data 123. This may be achieved for the "normal" dataset by multiplying the conversion factor obtained in 122 by the DRG weight at the admission level. For the data identified as outlier admissions, the admission level RRV may be calculated in the following manner: the upper outlier threshold (upper range of the LOS SD range) LOS value is multiplied by the conversion factor. For low volume admissions, the admission level RRV may be calculated by multiplying the median LOS by the overall conversion factor. The admission level RRV relating to ungroupable DRG's may be calculated by multiplying the actual LOS by the average billed per day amount.

Once the admission level modular RRV's are calculated, they may be allocated to the individual encounter level to take advantage of the fact that the actual episode data is at the encounter level 126. This allocation may use the paid amounts as the basis to avoid allocating any resource use to an encounter with a zero dollar paid amount. Allocation of the admission level RRV to the encounter level may be accomplished by utilizing the acute inpatient data initially extracted from the patient database in 112. As illustrated in FIG. 2, for a single admission comprising multiple encounters, each encounter within an admission is calculated as a percentage of the total admission 125 which is then multiplied by the admission RRV to create an encounter level adjusted RRV 126.

Figure 3:
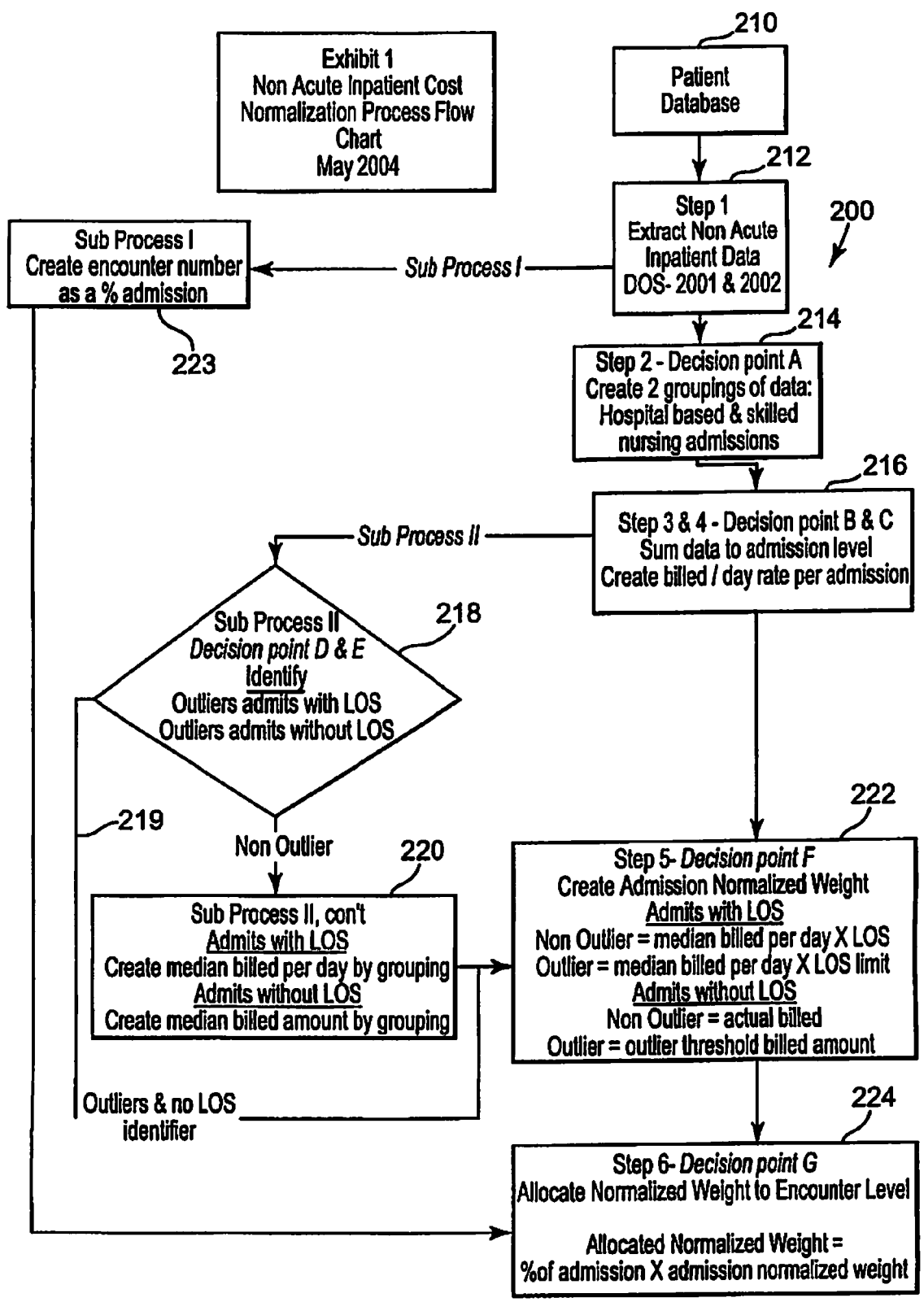
FIG. 3 is a flowchart illustrating a preferred embodiment for the non-acute inpatient module of the inventive method.

Referring now to FIG. 3, a preferred embodiment of the inventive method as applied to the non-acute inpatient efficiency measurement module is provided in flow chart form 200. This process begins with the provision of a patient database 210 with extraction of the relevant patient data 212. Thus, in this embodiment, non-acute inpatient data is retained while acute inpatient data is excluded and processed in accordance with the description provided above in connection with FIG. 2.

Following data extraction 212, two groups or classifications of data may be created based upon the type of admission: (1) hospital-based admissions; and (2) skilled nursing admissions 214. Such classification may be completed in a variety of ways. In the preferred embodiment, the billing code used on the industry-standard claim form is utilized and which may indicate a hospital-based admission or not. If not, the default classification may be skilled nursing admissions. This classification scheme may be advantageous since, inter alia, there is generally a reproducible differential in cost per day incurred between skilled nursing and hospital-based admissions.

After the data has been appropriately classified, both of the data sets are summed to the admission level 216. This is desirable because multiple encounters may be included within a single admission, therefore summing the data to admission level allows the admission to be evaluated in its entirety. During this process, admissions with a billed amount of $0 may be deleted from the two sets of classified data as they have no impact on the further analysis. Moreover, admissions with a negative billed amount may also be deleted from the data sets as these admissions are likely in the process of being adjusted and, left within the data set, will skew the results.

Unlike the acute inpatient process described above which uses DRG weighting, there is no weight scale specifically for non-acute inpatient matters. Thus, the Length of Stay (LOS) may be used as a base unit to measure resource use. Other equivalent base units may be readily apparent to those skilled in the art and are within the scope of the instant invention. The normalization process may use billed-per-day as the average amount of resources used per day for each admission 216. Admissions without an LOS may be normalized using the median billed per admission by admission grouping (skilled nursing or hospital based) 216.

Continuing with reference to FIG. 3, outlier identification may be the next process step 218 and may comprise identification of outliers with an associated LOS and outliers without an associated LOS. As described above in connection with the acute inpatient process of FIG. 2, a standard deviation range from the median LOS for each admission grouping may be created; preferably 6 SDs in width (+/−3 about the median), but other widths may be used as will be readily apparent to those skilled in the art. Preferably the lower $99^{th}$ percentile of the data is used in this analysis to, among other things, ensure normality of the data and statistical significance of the results. Other percentile levels are well within the scope of the inventive process. Thus, as with the acute inpatient process, admissions falling outside the established standard deviation range are considered outliers.

For admissions without an associated LOS, an appropriate SD range may be established (preferably with a width of 6 SD about the median, though other widths may be used) from the median billed amount for each admission grouping (hospital based vs. skilled nursing). The preferred data set to be used in calculating the median and range may be the lower $99^{th}$ percentile of data, though other percentile levels may be used. Thus, all admissions without an associated LOS that are outside the established standard deviation range are considered outliers. The outliers, both with and without LOS, are flagged for further analysis 219.

The inventive process may next develop a median billed rate by admission grouping (skilled nursing and hospital based) 220. For admissions with an associated LOS value, a median billed rate per day for each admission group is identified, after removal of the outliers identified as described above. For admissions without an associated LOS, a median billed amount for each admission group is identified after outlier removal.

Next, an admission level modular RRV may be calculated for each admission group 222. For non-outlier admissions with an LOS, the RRV=median billed per day multiplied by LOS. For outlier admissions with an LOS, the RRV=median billed per day multiplied by the upper threshold of the established LOS standard deviation range. For non-outlier admissions without an LOS, the RRV is assigned to be the actual billed amount. For outlier admissions without an LOS, the RRV will be the upper threshold of the established billed amount standard deviation range.

Once the admission level RRV's are calculated 222, they may be allocated to the individual encounter level to take advantage of the fact that the actual episode data is at the encounter level 224. This allocation may use the paid amounts as the basis to avoid allocating any resource use to an encounter with a zero dollar paid amount. Allocation of the admission level RRV to the encounter level may be accomplished by utilizing the acute inpatient data initially extracted from the patient database 210. As illustrated in FIG. 3, for a single admission with multiple encounters, each encounter within an admission is calculated as a percentage of the total admission 223 which is then multiplied by the admission RRV to create an encounter level modular RRV 224.

Figure 4:
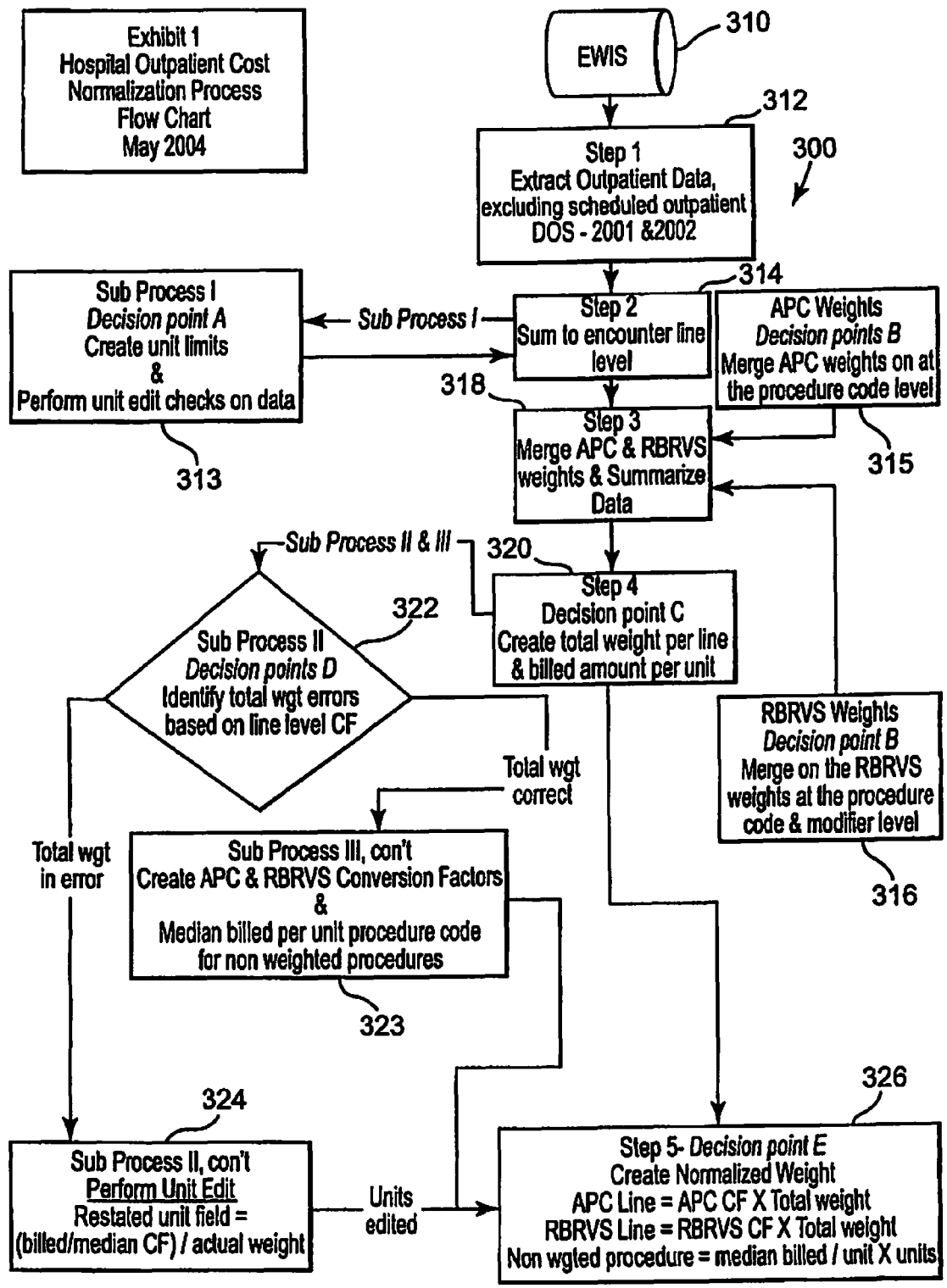
FIG. 4 is a flowchart illustrating a preferred embodiment for the hospital outpatient module of the inventive method.

With reference now to FIG. 4, a preferred embodiment of the inventive method as applied to the outpatient efficiency measurement module is provided in flow chart form 300. Initially, the process may provide a patient database 310 and extract outpatient data 312 similar to the extraction processes described above. To facilitate the significance of the results, scheduled outpatients may be identified and excluded from further analysis within this component. Scheduled outpatient efficiency measurement may be accomplished within a separate process component to be discussed in connection with FIG. 5 infra in combination with professional office-based service data. As will be discussed further, scheduled outpatient treatment plan options may be performed in either the outpatient or professional setting. To eliminate price as a confounding factor, a single normalization methodology must be used. Thus, the preferred embodiment for the outpatient component of care comprises only outpatient surgery and emergency room patients. This includes all outpatient encounters that do not have a room and board revenue code, but do contain a primary icd9 procedure code or an emergency room revenue code. Under the inventive process, all other outpatient treatment plan options may thus be classified and analyzed under the scheduled outpatient and professional services component. Those skilled in the art will recognize that alternate embodiments of the inventive process may include all scheduled outpatient services within the hospital outpatient normalization process, but such results will be subject to the limitations described above.

Returning now to FIG. 4, when the extraction of non-scheduled outpatient data is complete 312, unit limits may be created and unit edit checks may be performed 313. Unit editing is performed because the number of units billed has a direct correlation to the amount of resources attributed to the particular resource item. Thus, units must be accurate in order to create a valid measure of resource use. Unfortunately, not all hospital facilities are paid based on the number of units they bill, therefore they are less diligent in billing accurate units. Moreover, such facilities bill procedures/treatment plan options in different ways, e.g., 1 unit may be the equivalent of 1 minute of 15 minutes. Such billing differential may also occur from person to person within a given facility. To address these potentially inaccurate resource estimates, unit limits may be created and unit edit checks performed to more accurately reflect resource use.

Establishing a standard deviation range, preferable 6 (+/− 3) SDs around the median by procedure code, may create unit limits 313. This unit limit range may then be used to determine whether the unit field is in error, or perhaps incorrectly coded. Those skilled in the art will readily recognize that smaller or larger widths may be used for the SD range, all of which are within the scope of the inventive process. In calculating the upper and lower limits of the range, efforts may be used to ensure that statistically normal data may be included. Preferably, the middle $98^{th}$ percentile, or other percentile as deemed appropriate by those skilled in the art in alternate embodiments, of the available data be used to calculate the standard deviation limits, thus effectively cutting off the upper and lower 1% tails of the data set, respectively. Alternative data may, however, be selected by those skilled in the art depending upon the goals of the process. For example, the upper or lower $98^{th}$ percentile, or other percentiles, of the data may be used to eliminate any biased skewing of the data that may be present.

Unit edit checks 313 may be accomplished by comparison of the unit fields with the established range to identify the unit fields outside the upper or lower range limits. Those unit fields outside the upper limit are restated in accordance with description provided infra. Next, the data may be summed to the encounter level 314. This is done, inter alia, because a single encounter may have multiple services attached to it and the applicable weighting system for this component are applied at the service level.

The hospital outpatient normalization process may continue by merging the edited data on APC weights 315 and RBRVS weights 316. The combination of the two weighting systems allows for the majority of the relevant claims data to be normalized with a relative weighting system. The APC weights are merged with the data by procedure code and the RBRVS weights are merged with the data by procedure code and modifier. Thus, two groupings of data are created, based on either APC or RBRVS weighting 318. If data has procedure codes in common or shared between the APC and RBRVS weighting systems, the APC weight takes precedence in the preferred embodiment. Significantly, since the billed amounts and the weights for each system are kept separate, the RRV's produced will be relative to each other.

Next, billed amount per unit may be established. For APC related data, the billed amounts are applied to the APC weights 320. All RBRVS related services are normalized using the median RBRVS conversion factor.

A unit edit may be formed based on APC and RBRVS conversion factors. Creation of the APC and RBRVS conversion factors may proceed under various embodiments. Initially, encounters where units have been edited may be excluded, as are low volume APC and/or low volume RBRVS codes from the conversion factor calculation. Low volume APC/RBRVS codes are defined as the relevant codes having a statistically insignificant volume as well known and understood by those skilled in the art.

The APC conversion factor=sum (billed amount) divided by the sum (total APC weights).

The RBRVS conversion factor=sum (billed amount) divided by the sum (total RBRVS weights).

For non-weighted treatment plan options, use the median billed per unit=median (billed/unit) by procedure code.

Low volume treatment plan options normalized using the billed per unit methodology, i.e., those low volume treatment plan options that are non-weighted will have all of the relevant data considered when calculating the median billed per unit, not just the middle $98^{th}$ percentile, or other statistically significant range of data.

A total weight representing resource may be created for each treatment plan option 320. The overall weight for each treatment plan option comprises resources from three areas: units; weights (APC or RBRVS); and a discount factor. The units are defined as the number of times a treatment plan option is performed during the same encounter. The weight is defined as the amount of resources used to perform one instance (one unit) of that treatment plan option. The discount factor or rate is applied to the total weight when two or more services for the same treatment plan option are performed during the same incident or encounter. An example of a discount factor would be the performance of the same surgery, e.g., carpal tunnel surgery, on both the left and right hands, comprising two surgical "units." A single surgical unit may be defined in this instance as comprising surgical preparation and the surgery itself. The preparation resources used may be attributed and allocated to both surgeries, therefore the resource utilization used for the preparation for the two surgical units may be defined as one unit. Since there are two surgical units being performed (right and left hand), the second surgery should not include the resources used in the first surgery's preparation. Thus, the first surgical unit may receive full weighting comprising the preparation and surgery, while the second surgical unit may receive half weighting comprising the surgery component only.

In practice, the total weight for each encounter or treatment plan option is calculated by multiplying the number of services or treatment plan options performed (units) by the APC or RBRVS weight (as appropriate) by the discount rate/factor.

Thus, total weight=(APC weight or RBRVS weight)× units×discount factor.

The billed amount per unit of 320 may also be captured to evaluate the accuracy of the total weight calculation 322. If, for example, the total weight calculation for each encounter is inconsistent with the amount billed, the total weight, which represents resource use, may be adjusted.

Identification of inconsistency between the amount billed and the total weight calculated may be achieved by firstly calculating APC and RBRVS conversion factors 323. The APC conversion factor may be expressed as the summation of the billed amount divided by the summation of the total APC weights. The RBRVS conversion factor may similarly be expressed as the summation of the billed amount divided by the summation of the total RBRVS weights. Medians for each of the conversion factors (APC and RBRVS) may then be calculated and standard deviation ranges with the appropriate statistical significance may be obtained for each conversion factor. A preferred standard deviation range for each conversion factor (APC and RBRVS) may be biased so that the upper range, that is, the range above the median is 3 standard deviations and the lower range, that is the range below the median is 1 standard deviation. Other ranges or standard deviation widths may be used, including widths that are equally distributed about the median as appropriate and as recognized by one skilled in the art, depending upon the statistical goal required and are all within the scope of the inventive process. The range limits may be calculated using statistically valid procedures, e.g., use of only the middle $98^{th}$ percentile of the data, i.e., the "normal" data, may be used. Thus, the upper and lower 1% of the data may be excluded from calculation of the range limits. One skilled in the art may elect to use other definitions of data normality under the inventive process.

Comparison of the unit fields with the established standard deviation range will identify those units that are outside the range. The units identified as outside the established standard deviation range may be edited and restated as the median of the billed APC conversion factor divided by the appropriate APC weight 324. Where the restated unit calculation results in a value less than one (1), they are reset or defaulted to one (1). Then, the total weight is recalculated using the restated units, i.e., total weights=units (restated)×weight.

A median billed amount per unit may also be created by identifying the median billed amount per unit by procedure code for those procedures/treatment plan options not having weighting (APC or RBRVS) associated with them 323.

Since there are two groupings of data, one for APC and one for RBRVS weighted encounters, two overall conversion factors are created in 323. Encounters where the units were edited and the low volume APC and low volume RBRVS codes may be excluded from the conversion factor calculation to facilitate or improve statistical significance of the results. The APC conversion factor 323 is calculated by dividing the summation of the billed amounts by the summation of total APC weights. The RBRVS conversion factor 323 is calculated by dividing the summation of the billed amount by the summation of total RBRVS weights. Low volume treatment plan options may be defined as those not present in a statistically significant number as that terminology is well understood by those skilled in the art. Such low volume procedures normalized under the inventive process using the billed per unit by procedure code methodology may have all data considered when calculating the median billed per unit by treatment plan option, not just the middle $98^{th}$ percentile, although as those skilled in the art will readily recognize, it may be possible and perhaps even beneficial to eliminate a certain percentage, e.g., 1%, from the upper and lower ends of the data distribution.

Ultimately, the hospital outpatient modular RRV is calculated at 326. For APC procedures, the RRV=APC conversion factor multiplied by the total weight. For RBRVS procedures, the RRV=RBRVS conversion factor multiplied by the total weight. For non-weighted procedures, the RRV=the median billed per unit multiplied by the units.

Figure 5:
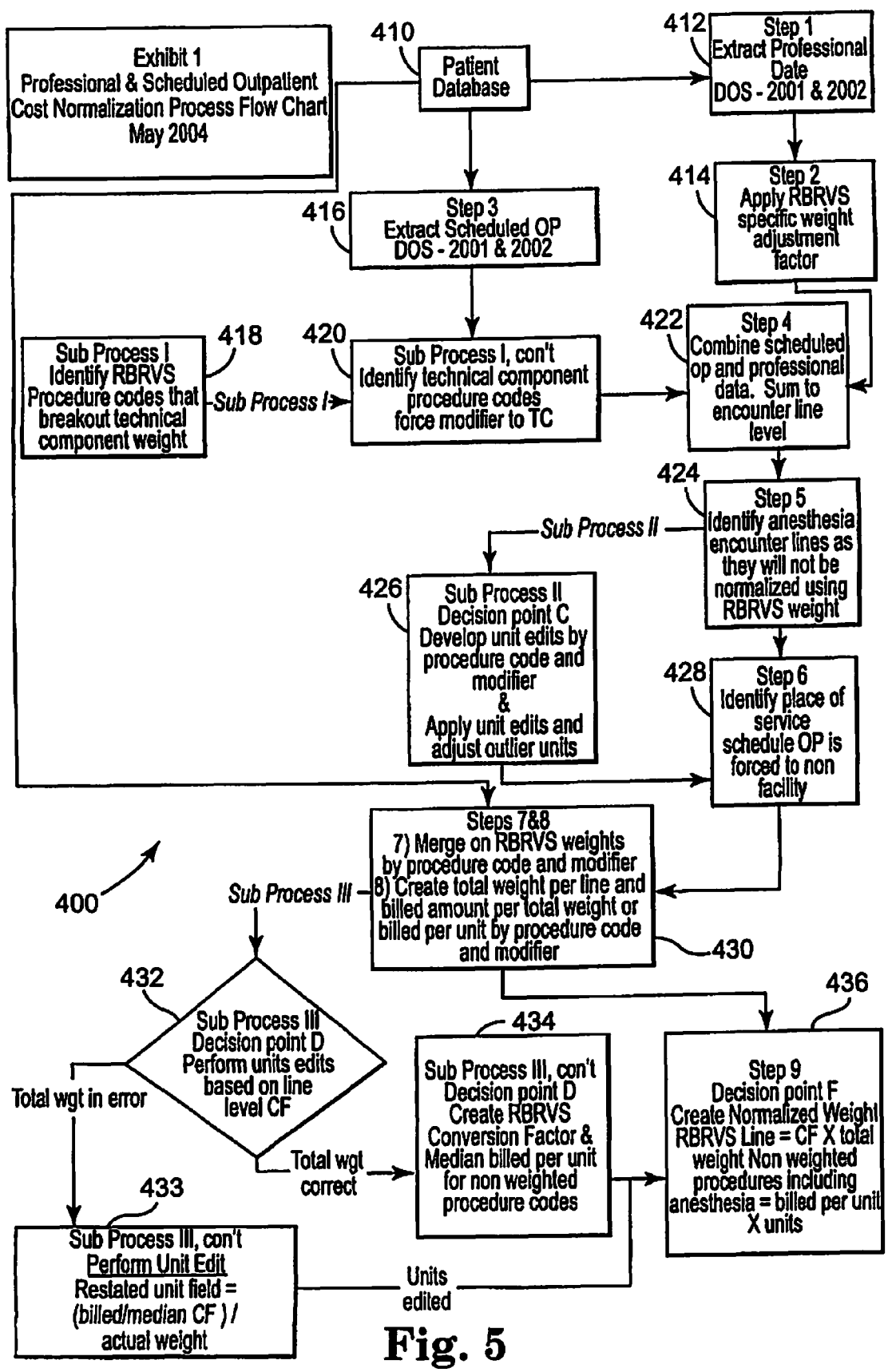
FIG. 5 is a flowchart illustrating a preferred embodiment for the professional office-based and scheduled outpatient module of the inventive method.

Turning now to FIG. 5, the process flow for an embodiment of the instant invention illustrating normalization of the professional office-based component of care, including scheduled outpatient care comprising outpatient surgery and emergency room treatment plan options, is provided. This module may develop an RRV that is relative to the other components of care and that measures resource use for a "normal" professional office-based or scheduled outpatient hospital service. As described in connection with the outpatient hospital service module, scheduled outpatient in this context may be further defined as all encounters from a hospital that do not have a room and board revenue code, but that do have a primary ICD9 procedure code or an emergency room revenue code. All other outpatient treatment plan options/procedures default to the scheduled outpatient category.

Since the scheduled outpatient treatment plan option may be performed in either a professional office or in a hospital outpatient setting, the scheduled outpatient data will be normalized along with the professional office-based data. Generally, the RBRVS weighting system and billed amount may be used to determine relative resource use for each treatment plan option. If an RBRVS weight does not exist for a particular treatment plan option, the median billed per unit may be used for the normalization methodology.

The RBRVS is, as discussed above, a schedule of uniform relative values that indicate the amount of resources that services use. Such RBRVS may vary by the location where the service was performed and the entity or person submitting the bill. Thus, generally speaking, a single treatment plan option code may include up to 4 different weight values: non-facility weight; facility weight; technical component weight; and professional component weight.

Non-facility weight may be defined as the weight attributed to a service performed in a professional provider of medical care and wherein the bill relating to the associated encounter is submitted by the professional provider.

Facility weight may be defined as the weight attributed to a service that is performed in a hospital.

Technical component weight may be defined as the weight applied to the hospital's supplied services where an independent professional performed the service.

Professional component weight may be defined as the weight attributed to the professional provider of care when the provider performed the service in a hospital.

In practice, if a procedure/treatment plan option code has a technical component broken out, then the scheduled outpatient encounters are assumed to by the technical component and, therefore, receive the technical component weight. It may be assumed that the professional performing the subject service may submit a separate bill for the professional component relating to that service.

Alternatively, if a treatment plan option code does not have a technical component broken out and there is a difference between the facility and non-facility weights, then the scheduled outpatient may receive the non-facility weight. This is done because the relevant treatment plan option should receive the same weight that it would receive should it be performed in a professional office setting. Thus, the same service receives the same weight.

Professional encounters may receive the facility, non-facility, or professional component weight depending upon the place of service. It may be assumed that if a service is performed in a facility, then the facility will also bill the technical component of that service.

Referring specifically now to FIG. 5, the professional office-based and scheduled outpatient module 400 begins, as the other modules begin, with the provision of a patient database 410 extraction of the appropriately categorized data therefrom 412. Since there are two data types required for this module, two extractions may be executed; the first process extracting professional office-based data and the second process extracting scheduled outpatient data.

With regard to the professional data thus extracted, the next step may be to apply RBRVS specific weight adjustments to specific modifiers 414. This is a desirable procedure because certain modifiers may indicate a slight difference in the treatment plan option being performed when compared with a "normal" treatment plan option. Thus, an adjustment may be applied to reflect the actual resources used to perform the service.

Next, the scheduled outpatient data may be extracted 416 from the patient database 410. Then, all RBRVS procedure codes having a technical component breakout may be identified 418 from the patient database 410. The modifiers may be forced to technical component 420. Then the professional data from 414 and the scheduled outpatient data may be combined and summed to the encounter line level 422. This combination and summation procedure factors in the adjustments to encounters that affect the payment and utilization data fields. In addition, the RBRVS weighting system may be applied at the procedure/service, i.e., encounter, level. Further, one encounter may have many services.

Anesthesia data may also be identified 424. This is important because RBRVS weighting does not apply to anesthesia services, instead such services may be normalized using the median billed per unit methodology as will be more fully described below.

A next step in the process may be performing unit edits 426. Here, as with previously described modules, a standard deviation (SD) range, preferably +/−3 SDs about the median though other widths may be used, by procedure code and modifier to determine if a particular unit field is in error or incorrectly coded. Various statistical manipulation of the data may be used by those skilled in the art. For example, the upper 1% of data may be deleted before calculating the SD range to enhance the statistical value of the unit edit. Unit fields identified as being outside the upper limit of the SD range may be restated to be the equivalent of the upper limit of the SD range.

Once the unit field edit has been completed, the place/location of the individual services may be identified 428. This is important because for the professional services, location of performance of service dictates whether the RBRVS facility or non-facility weight is used. Scheduled outpatient receives the non-facility weight.

Next, the data is merged on the RBRVS weights by place/location of service, procedure code and by modifier 430. Where applicable, the scheduled outpatient receives the technical component of the RBRVS weight. Alternatively, the scheduled outpatient receives the non-facility weight.

A total weight per line and billed amount per weight may also be created 430. Alternatively, a billed per unit by procedure code and modifier may be created. In this connection, it is important to note that the same service may be performed multiple times, therefore the number of units has a large impact on the total weight. Thus, the total weights for a line should reflect resource use. Total Weight may be expressed as the product of the RBRVS weight, the number of units and the modifier factor, i.e., Total Weight=RBRVS weight×Units×Modifier Factor.

Next a unit edit may be performed 432. First, the total weight or resource use for the encounter line may be adjusted or restated if inconsistent with the amount billed 433. This may be achieved by establishing a standard deviation range, preferably 3SD above the median billed effective conversion factor and 1SD below the median billed effective conversion factor. Statistically, the results may be enhanced by including only the middle 98 percentile of data when calculating the limit thresholds, however more or less data may be retained depending upon the desired results as known by those skilled in the art. Ultimately, the unit fields identified as being outside the established SD range limits may be restated as follows:

Restated units=(billed amount÷median conversion factor) ÷RBRVS weight.

The total weight may also be recalculated as follows:

Total weights=units×weight.

The conversion factor may be created by excluding encounters where the units have been edited and restated as described above. Moreover, low volume RBRVS codes, i.e., statistically insignificant numbers of RBRVS as understood by those skilled in the art, may also be excluded from the conversion factor calculation 434.

The RBRVS conversion factor=summation of the billed amount÷summation of the total RBRVS weights.

The median billed per unit=median (billed/unit) by procedure code and modifier. Note that low volume treatment plan options/procedures identified herein will have all associated data considered when calculating the median billed per unit, not just the middle $98^{th}$ percentile of the data as discussed above.

Ultimately, the modular RRV is created 436. For weighted treatment plan options, the total weight for an encounter line is multiplied by the RBRVS conversion factor to create the RRV. For non-weighted treatment plan options, including anesthesia, the RRV is calculated by multiplying the units by the median billed per unit rate for the respective treatment plan options.

Figure 6:
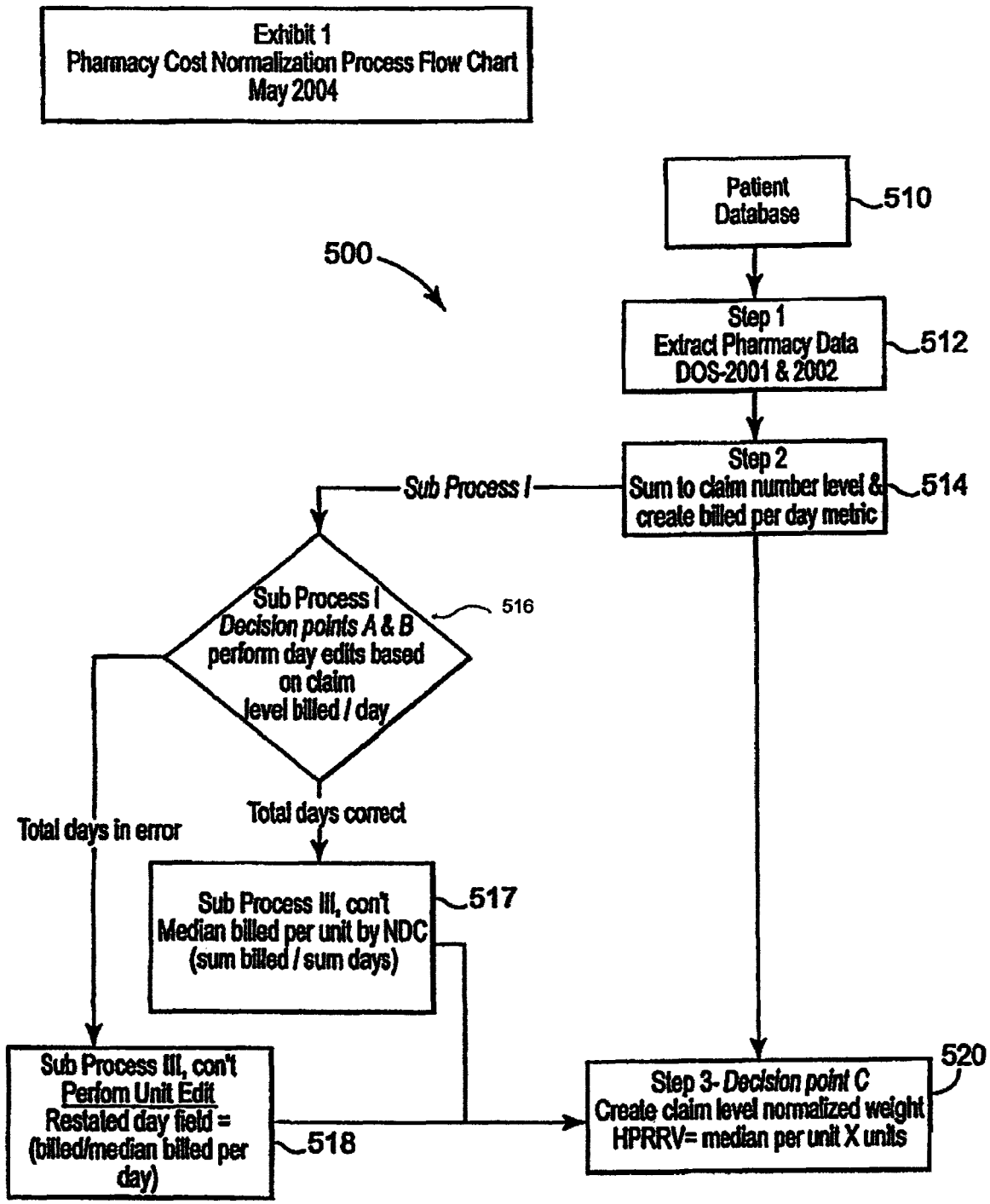
FIG. 6 is a flowchart illustrating a preferred embodiment for the pharmacy module of the inventive method.

With reference now to FIG. 6, the process flow for a preferred embodiment of the invention illustrating normalization of the pharmacy component of care module is provided 500.

This process may develop an RRV value that measures resource use for a "normal" prescription. Since there is no relative weighting scale for prescription drugs, e.g., APC or DRG, the median billed amount per day by NDC may be used to normalize the pharmacy component of care. The billed amount per day metric may be used to validate that the number of days assigned to the prescription are within an acceptable range. If this metric is determined to be outside the acceptable range, the number of days may be adjusted so that the billed per day amount is the equivalent of the median billed per day amount for that NDC.

Initially, the process begins with extraction of pharmacy claims data 512 from the patient database 510. Such data may comprise all prescriptions filled by a pharmacist as well as those obtained via mail order methods. The billed amount may be the equivalent of the sum of the calculated ingredient cost plus dispensing fee plus sales or other tax. Calculating the billed amount in this manner ensures that the RRV is relative between the NDS's and with the other components of care.

After extraction and calculation of the billed amount, the data is summed to claim number level and a billed per day value is created by dividing the billed amount calculated as described above by the number of days assigned to the prescription 514. Based on the billed per day results, a median billed per day value and standard deviation thereof calculated so that an acceptable range may be created. Preferably the standard deviation range comprises 3 SD above the median and 1 SD below the median billed per day may be used. Those skilled in the art may recognize that the width and distribution of the SD range about the median may vary depending upon the analysis goal. Moreover, the middle $98^{th}$ percentile of the billed per day data is preferably used, though other percentile selections are well within the scope of the invention.

The billed per day metric may then be compared with the acceptable range. If the billed per day value is outside the established acceptable range, the number of days will be adjusted so that an edited billed per day value is created to be equivalent in value to the median billed per day for the relevant NDC 516. Restatement of the outlying data may be achieved by dividing the actual billed amount by the median billed per day by NDC 517.

Low volume NDCs are identified and restated 518. Preferably, NDCs with less than 5 prescriptions may be flagged as low volume. Generally, the standard for setting a low volume limit is that of statistical significance and, as a result, those skilled in the art may require more or allow fewer prescriptions per NDC before categorizing them as low volume.

The modular RRVs may then be calculated 520. The RRVs for data not identified as low volume may be calculated as the median billed per day for the respective NDC code multiplied by the number of days for the relevant claim. Low volume NDC code RRV calculation may be accomplished by multiplying the median billed per day rate (using all available data) by the number of days for the relevant claim.

One embodiment of the invention further comprises the accommodation of efficient preventive care and chronic care management in the efficiency model described herein. Preventive care and appropriate chronic care monitoring and management are desirable to minimize unnecessary complications and the treatments associated therewith. Thus, the inventive efficiency measure described herein does not penalize providers who provide appropriate levels of preventive and/or chronic care monitoring and management. Similarly, the invention does not reward providers who underutilize these appropriate methods of care.

Thus, one component of the invention described herein allows the user to make choices from several options including, inter alia:

(1) Reward or neutralize for appropriate use of preventive care and chronic care management and/or monitoring;

(2) Penalize or neutralize for underuse of preventive care and chronic care management and/or monitoring; and (3) Penalize or neutralize for overuse of preventive care and chronic care management and/or monitoring.

This system is implemented through a combination of patient classification according to needs—by age, gender, conditions and other self-reported patient information including behavior (physical activity, diet and the like), and family history. The classification scheme is cross-referenced against evidence-based best practice care standards well known to those skilled in the art. This, in turn, identifies the appropriate type, timing and frequency of preventive care and chronic care management and/or monitoring services required for efficient and effective quality of care. The results from this classification scheme are merged with grouped claim data after the RRV assignment described herein. Thus, after this merger, the user may decide from the at least three options provided above.

The invention having been described, examples will now be provided to further illustrate the inventive method. Reference numerals are provided and will refer back to the appropriate Figures.

Example 1

Inpatient Acute Cost Normalization

With specific reference to FIG. 2, and in accordance with steps 112 and 123 therein, the following exemplary data is provided:

| DRG Code | Admission # | Facility | Encounter # | Admit Count | LOS | Billed | Paid | % of Admission |
|---|---|---|---|---|---|---|---|---|
| 430 | 1 | Hos A | 1 | 1 | 5 | 2295 | 1606 | 21.7 |
| 430 | 1 | Hos A | 2 | 0 | 18 | 8262 | 5783 | 78.3 |

Next, in accordance with steps 114, 116 and 118 wherein the data is summed to the admission level, merged on weights and the total DRG case data weight is calculated using the formula:

Total Weight=DRG Day 1 Weight=((LOS−1)×DRG Day 2 Weight.

| DRG Code | Admission # | Facility | DRG Day 1 Weight | DRG Day 2 Weight | Admit Count | Billed | Paid | Total Weight |
|---|---|---|---|---|---|---|---|---|
| 430 | 1 | Hos A | 0.4834987 | 0.3288348 | 1 | 10557 | 7389 | 7.717863 |

The conversion factor may now be calculated according to step 122 in FIG. 2, utilizing all data in process, excluding outliers and low volume data as described herein.

Thus, IP Acute Rate: 4,543.21; the Billed Amount is 2,641,762,527; and the total DRG Weights is 581,475.

Next, the RRV may be calculated as follows, using the formula RRV=CF×Total DRG Weights, correspondent with step 124 in FIG. 2:

| DRG Code | Admission # | Facility | Encounter | Admit Count | LOS | Billed | Paid | Total Weight |
|---|---|---|---|---|---|---|---|---|
| 430 | 1 | Hos A | 1 | 1 | 5 | 10557 | 7389 | 7.717863 |
| 430 | 1 | Hos A | 2 | | 18 | | | |

Thus, the RRV is calculated to be 35,063.86.

Finally, the data may be allocated to the encounter level from the admission level as described in connection with FIG. 2, ref. no. 126 as follows:

| DRG Code | Admission # | Facility | Encounter | Admit Count | LOS | Billed | Paid | % of Paid on Admit | Allocated RRV |
|---|---|---|---|---|---|---|---|---|---|
| 430 | 1 | Hos A | 1 | 1 | 5 | 2295 | 1606.5 | 22% | 7622.58 |
| 430 | 1 | Hos A | 2 | 0 | 18 | 8262 | 5783.4 | 78% | 27441.28 |
| | | | | | | TOTAL | 7389.9 | 100% | 35063.86 |

Example 2

Inpatient Non-Acute Cost Normalization

This example corresponds with FIG. 3.

The following data is provided with specific reference to reference numerals 212 and 214, wherein the data is extracted from the database and two groupings of data created, either Hospital Based or Skilled Nursing admissions.

| Admit Type | Admission # | Facility | Encounter # | LOS | Billed | Paid | % of Paid |
|---|---|---|---|---|---|---|---|
| Skilled Nurse | 1 | Facility B | 1 | 0 | 0 | 0 | 0% |
| Skilled Nurse | 1 | Facility B | 2 | 0 | 0 | 0 | 0% |
| Skilled Nurse | 1 | Facility B | 3 | 0 | 0 | 0 | 0% |
| Skilled Nurse | 1 | Facility B | 4 | 15 | 4991 | 1642 | 25% |
| Skilled Nurse | 1 | Facility B | 5 | 29 | 10360 | 3175 | 48% |
| Skilled Nurse | 1 | Facility B | 6 | 17 | 5897 | 1861 | 28% |

Next, the data is summed to admission level using the formula: in accordance with step 216:

| Admit Type | Admission # | Facility | Encounter # | LOS | Billed | Paid | Billed per day |
|---|---|---|---|---|---|---|---|
| Skilled Nurse | 1 | Facility B | N/A | 61 | 21,248 | 6,679.50 | 348.34 |

Then, in accordance with step 218, outlier LOS limits may be calculated, not shown here.

The rate per day may then be calculated using all data, exclusive of outliers and low volume data as described herein and with reference to step 220. Thus, the Median Skilled Nursing Rate per Day may be calculated as: 370.00.

The RRV may now be calculated using the formula:

RRV=CF×LOS as described in step 222 and further illustrated below:

| Admit Type | Admission # | Facility | Encounter # | LOS | Billed | Paid | RRV |
|---|---|---|---|---|---|---|---|
| Skilled Nurse | 1 | Facility B | N/A | 61 | 21248 | 6679 | 22,570 |

Ultimately, the data may be allocated to the encounter level from the admission level as described in steps 224 and 219 and illustrated below:

| Admit Type | Admission # | Facility | Encounter # | LOS | Billed | Paid | % of Paid on Admit | Allocated RRV |
|---|---|---|---|---|---|---|---|---|
| Skilled Nurse | 1 | Facility B | 1 | 0 | 0 | 0 | 0% | — |
| Skilled Nurse | 1 | Facility B | 2 | 0 | 0 | 0 | 0% | — |
| Skilled Nurse | 1 | Facility B | 3 | 0 | 0 | 0 | 0% | — |
| Skilled Nurse | 1 | Facility B | 4 | 15 | 4991 | 1642 | 25% | 5,550 |
| Skilled Nurse | 1 | Facility B | 5 | 29 | 10360 | 3175 | 48% | 10,730 |
| Skilled Nurse | 1 | Facility B | 6 | 17 | 5897 | 1861 | 28% | 6,290 |
| | | | TOTAL | 61 | 21248 | 6679 | 100% | 22,570 |

Example 3

Hospital Outpatient Cost Normalization

This example corresponds with FIG. 4, reference numeral correspondence will be noted throughout the illustration.

First, outpatient data is extracted according to step 312 and summed to encounter line level (314) as follows:

| Admit Type | Encounter # | Line # | Facility | CPT CODE | MODIFIER | UNITS | BILLED | Paid |
|---|---|---|---|---|---|---|---|---|
| Hospital OP | 1243567850 | 1 | Facility A | J2550 | ~ | 1 | 37.85 | — |
| Hospital OP | 1243567850 | 2 | Facility A | J2270 | ~ | 1 | 36.96 | — |
| Hospital OP | 1243567850 | 3 | Facility A | J2765 | ~ | 1 | 36.73 | 24.17 |
| Hospital OP | 1243567850 | 4 | Facility A | Q0081 | ~ | 1 | 608.50 | 194.35 |
| Hospital OP | 1243567850 | 5 | Facility A | G0001 | ~ | 1 | 22.00 | 20.07 |
| Hospital OP | 1243567850 | 6 | Facility A | 80048 | ~ | 1 | 287.00 | 67.73 |
| Hospital OP | 1243567850 | 7 | Facility A | 85027 | ~ | 1 | 150.00 | 60.20 |
| Hospital OP | 1243567850 | 8 | Facility A | 87186 | ~ | 1 | 136.00 | 77.76 |
| Hospital OP | 1243567850 | 9 | Facility A | 87077 | ~ | 1 | 41.00 | 105.35 |
| Hospital OP | 1243567850 | 10 | Facility A | 87086 | ~ | 1 | 128.28 | 85.29 |
| Hospital OP | 1243567850 | 11 | Facility A | 87491 | ~ | 1 | 128.00 | 273.42 |
| Hospital OP | 1243567850 | 12 | Facility A | 87591 | ~ | 1 | 128.00 | 273.42 |
| Hospital OP | 1243567850 | 13 | Facility A | 87088 | 59 | 1 | 119.00 | 78.30 |
| Hospital OP | 1243567850 | 14 | Facility A | 87210 | ~ | 1 | 45.00 | 40.13 |
| Hospital OP | 1243567850 | 15 | Facility A | 81025 | ~ | 1 | 238.24 | 55.18 |
| Hospital OP | 1243567850 | 16 | Facility A | 81003 | ~ | 1 | 87.70 | 30.10 |
| Hospital OP | 1243567850 | 17 | Facility A | 74160 | ~ | 1 | 1,185.95 | 543.08 |
| Hospital OP | 1243567850 | 18 | Facility A | 72193 | ~ | 1 | 554.48 | 543.08 |
| Hospital OP | 1243567850 | 19 | Facility A | 99283 | 25 | 1 | 416.50 | 247.04 |
| Hospital OP | 1243567850 | 20 | Facility A | 90784 | ~ | 3 | 379.50 | 337.20 |
| | | | | | | | 4,766.69 | 3,055.87 |

Next, according to steps 318, 320, 313, 315 and 316, the data may be summed to admission level, units tested and a total weight created, according to the formula:

Total Weight=Weight×Units×Discount.

| Admit Type | Encounter # | Line # | Facility | CPT Code | Modifier | Units | Billed | Paid | APC Wgt | RVU Wgt | Reprice Method | Discount Factor | Total WT |
|---|---|---|---|---|---|---|---|---|---|---|---|---|---|
| Hospital OP | 1243567850 | 1 | Facility A | J2550 | ~ | 1 | 37.85 | — | | 0.01 | APC repriced | 1 | 0 |
| Hospital OP | 1243567850 | 2 | Facility A | J2270 | ~ | 1 | 36.96 | — | | 0.03 | APC repriced | 1 | 0 |
| Hospital OP | 1243567850 | 3 | Facility A | J2765 | ~ | 1 | 36.73 | 24.17 | | 0.04 | APC repriced | 1 | 0 |
| Hospital OP | 1243567850 | 4 | Facility A | Q0081 | ~ | 1 | 608.50 | 194.35 | 1.81 | 1.74 | APC repriced | 1 | 1.81 |
| Hospital OP | 1243567850 | 5 | Facility A | G0001 | ~ | 1 | 22.00 | 20.07 | | 0.17 | RBRVS repriced | 1 | 0.17 |
| Hospital OP | 1243567850 | 6 | Facility A | 80048 | ~ | 1 | 287.00 | 67.73 | | 0.27 | RBRVS repriced | 1 | 0.27 |
| Hospital OP | 1243567850 | 7 | Facility A | 85027 | ~ | 1 | 150.00 | 60.20 | | 0.24 | RBRVS repriced | 1 | 0.24 |
| Hospital OP | 1243567850 | 8 | Facility A | 87186 | ~ | 1 | 136.00 | 77.76 | | 0.31 | RBRVS repriced | 1 | 0.31 |
| Hospital OP | 1243567850 | 9 | Facility A | 87077 | ~ | 1 | 41.00 | 105.35 | | 0.42 | RBRVS repriced | 1 | 0.42 |
| Hospital OP | 1243567850 | 10 | Facility A | 87086 | ~ | 1 | 128.28 | 85.29 | | 0.34 | RBRVS repriced | 1 | 0.34 |
| Hospital OP | 1243567850 | 11 | Facility A | 87491 | ~ | 1 | 128.00 | 273.42 | | 1.09 | RBRVS repriced | 1 | 1.09 |
| Hospital OP | 1243567850 | 12 | Facility A | 87591 | ~ | 1 | 128.00 | 273.42 | | 1.09 | RBRVS repriced | 1 | 1.09 |
| Hospital OP | 1243567850 | 13 | Facility A | 87088 | 59 | 1 | 119.00 | 78.30 | | 0.33 | RBRVS repriced | 1 | 0.33 |
| Hospital OP | 1243567850 | 14 | Facility A | 87210 | ~ | 1 | 45.00 | 40.13 | | 0.16 | RBRVS repriced | 1 | 0.16 |
| Hospital OP | 1243567850 | 15 | Facility A | 81025 | ~ | 1 | 238.24 | 55.18 | | 0.22 | RBRVS repriced | 1 | 0.22 |
| Hospital OP | 1243567850 | 16 | Facility A | 81003 | ~ | 1 | 87.70 | 30.10 | | 0.12 | RBRVS repriced | 1 | 0.12 |
| Hospital OP | 1243567850 | 17 | Facility A | 74160 | ~ | 1 | 1,185.95 | 543.08 | 4.75 | 8.18 | APC repriced | 1 | 4.75 |
| Hospital OP | 1243567850 | 18 | Facility A | 72193 | ~ | 1 | 554.48 | 543.08 | 4.75 | 8.04 | APC repriced | 1 | 4.75 |
| Hospital OP | 1243567850 | 19 | Facility A | 99283 | 25 | 1 | 416.50 | 247.04 | 2.66 | 1.58 | APC repriced | 1 | 2.66 |
| Hospital OP | 1243567850 | 20 | Facility A | 90784 | ~ | 3 | 379.50 | 337.20 | 0.83 | 0.49 | APC repriced | 1 | 2.49 |

Next, the non-APC lines billed amount may be allocated to APC paid lines by APC weight; total weight errors may be identified and restated units and total weights in accordance with steps 322 and 324 as follows:

| Encounter # | Line # | Billed | Paid | APC Wgt | RVU Wgt | Reprice Method | Discount Factor | Restated Total Weight | Allocated Billed | Upper CF Limit | Lower CF Limit | Actual CF | CF Edit Flag | Restate Units |
|---|---|---|---|---|---|---|---|---|---|---|---|---|---|---|
| 1243567850 | 1 | 37.85 | — | 0 | 0.01 | APC Repriced | 1 | 0 | — | | | | | |
| 1243567850 | 2 | 36.96 | — | 0 | 0.03 | APC Repriced | 1 | 0 | — | | | | | |
| 1243567850 | 3 | 36.73 | 24.17 | 0 | 0.04 | APC Repriced | 1 | 0 | — | | | | | |
| 1243567850 | 4 | 608.50 | 194.3 | 1.81 | 1.74 | APC Repriced | 1 | 1.81 | 620.77 | 528.5 | 44.20 | 342.96 | NORMAL | 1.0 |
| 1243567850 | 5 | 22.00 | 20.07 | 0 | 0.17 | RBRVS Repriced | 1 | 0.17 | 22.00 | 824.5 | 20.00 | 129.41 | NORMAL | 1.0 |
| 1243567850 | 6 | 287.00 | 67.73 | 0 | 0.27 | RBRVS Repriced | 1 | 0.27 | 287.00 | 824.5 | 20.00 | 1,062.9 | CF EDIT UPPER | 5.4 |
| 1243567850 | 7 | 150.00 | 60.20 | 0 | 0.24 | RBRVS Repriced | 1 | 1.46 | 150.00 | 824.5 | 20.00 | 102.16 | NORMAL | 1.0 |
| 1243567850 | 8 | 136.00 | 77.76 | 0 | 0.31 | RBRVS | | 0.31 | 136.00 | 824.5 | 20.00 | 438.71 | NORMAL | 1.0 |

| Encounter # | Line # | Billed | Paid | APC Wgt | RVU Wgt | Reprice Method | Discount Factor | Restated Total Weight | Allocated Billed | Upper CF Limit | Lower CF Limit | Actual CF | CF Edit Flag | Restate Units |
|---|---|---|---|---|---|---|---|---|---|---|---|---|---|---|
| 1243567850 | 9 | 41.00 | 105.3 | 0 | 0.42 | RBRVS Repriced | 1 | 0.42 | 41.00 | 824.5 | 20.00 | 97.62 | NORMAL | 1.0 |
| 1243567850 | 10 | 128.28 | 85.29 | 0 | 0.34 | RBRVS Repriced | 1 | 0.34 | 128.28 | 824.5 | 20.00 | 377.29 | NORMAL | 1.0 |
| 1243567850 | 11 | 128.00 | 273.4 | 0 | 1.09 | RBRVS Repriced | 1 | 1.09 | 128.00 | 824.5 | 20.00 | 117.43 | NORMAL | 1.0 |
| 1243567850 | 12 | 128.00 | 273.4 | 0 | 1.09 | RBRVS Repriced | 1 | 1.09 | 128.00 | 824.5 | 20.00 | 117.43 | NORMAL | 1.0 |
| 1243567850 | 13 | 119.00 | 78.30 | 0 | 0.33 | RBRVS Repriced | 1 | 0.33 | 119.00 | 824.5 | 20.00 | 360.61 | NORMAL | 1.0 |
| 1243567850 | 14 | 45.00 | 40.13 | 0 | 0.16 | RBRVS Repriced | 1 | 0.16 | 45.00 | 824.5 | 20.00 | 281.25 | NORMAL | 1.0 |
| 1243567850 | 15 | 238.24 | 55.18 | 0 | 0.22 | RBRVS Repriced | 1 | 1.21 | 238.24 | 824.5 | 20.00 | 195.46 | CF EDIT UPPER | 5.5 |
| 1243567850 | 16 | 87.70 | 30.10 | 0 | 0.12 | RBRVS Repriced | 1 | 0.12 | 87.70 | 824.5 | 20.00 | 730.83 | NORMAL | 1.0 |
| 1243567850 | 17 | 1,185.9 | 543.0 | 4.75 | 8.18 | APC Repriced | 1 | 4.75 | 1,218.14 | 528.5 | 44.20 | 256.45 | NORMAL | 1.0 |
| 1243567850 | 18 | 554.48 | 543.0 | 4.75 | 8.04 | APC Repriced | 1 | 4.75 | 586.67 | 528.5 | 44.20 | 123.51 | NORMAL | 1.0 |
| 1243567850 | 19 | 416.50 | 247.0 | 2.66 | 1.58 | APC Repriced | 1 | 2.66 | 434.53 | 528.5 | 44.20 | 163.36 | NORMAL | 1.0 |
| 1243567850 | 20 | 379.50 | 337.2 | 0.83 | 0.49 | APC Repriced | 1 | 2.49 | 396.37 | 528.5 | 44.20 | 159.19 | NORMAL | 3.0 |

Next, overall rates are created for APC and RVU Conversion Factors according to step 323. Thus:

| Encounter Type | Billed | Total Weights | Overall Rate |
|---|---|---|---|
| APC | 772,439,902 | 4,468,328 | 172.87 |
| RPC | 64,397,930 | 357,631 | 180.07 |

And finally, according to step 326, the RRV is created using the formula:

$$RRV = \text{Total Weight} \times \text{Conversion Factor}.$$

| Line # | Billed | Paid | APC Wgt | RVU Wgt | Reprice Method | Discount Factor | Restated Total Weight | Allocated Billed | Upper CF Limit | Lower CF Limit | Actual CF | CF Edit Flag | Restated Units | RRV |
|---|---|---|---|---|---|---|---|---|---|---|---|---|---|---|
| 1 | 37.85 | — | 0 | 0.01 | APC Repriced | 1 | 0 | — | | | | | | — |
| 2 | 36.96 | — | 0 | 0.03 | APC Repriced | 1 | 0 | — | | | | | | — |
| 3 | 36.73 | 24.17 | 0 | 0.04 | APC Repriced | 1 | 0 | — | | | | | | — |
| 4 | 608.50 | 194.3 | 1.81 | 1.74 | APC Repriced | 1 | 1.81 | 620.77 | 528.5 | 44.20 | 342.96 | NORMAL | 1.0 | 312.89 |
| 5 | 22.00 | 20.07 | 0 | 0.17 | RBRVS Repriced | 1 | 0.17 | 22.00 | 824.5 | 20.00 | 129.41 | NORMAL | 1.0 | 30.61 |
| 6 | 287.00 | 67.73 | 0 | 0.27 | RBRVS Repriced | 1 | 0.27 | 287.00 | 824.5 | 20.00 | 1,062.9 | CF EDIT UPPER | 5.4 | 48.62 |
| 7 | 150.00 | 60.20 | 0 | 0.24 | RBRVS Repriced | 1 | 1.46 | 150.00 | 824.5 | 20.00 | 102.16 | NORMAL | 1.0 | 264.40 |
| 8 | 136.00 | 77.76 | 0 | 0.31 | RBRVS Repriced | 1 | 0.31 | 136.00 | 824.5 | 20.00 | 438.71 | NORMAL | 1.0 | 55.82 |
| 9 | 41.00 | 105.3 | 0 | 0.42 | RBRVS Repriced | 1 | 0.42 | 41.00 | 824.5 | 20.00 | 97.62 | NORMAL | 1.0 | 75.63 |
| 10 | 128.28 | 85.29 | 0 | 0.34 | RBRVS Repriced | 1 | 0.34 | 128.28 | 824.5 | 20.00 | 377.29 | NORMAL | 1.0 | 61.22 |
| 11 | 128.00 | 273.4 | 0 | 1.09 | RBRVS Repriced | 1 | 1.09 | 128.00 | 824.5 | 20.00 | 117.43 | NORMAL | 1.0 | 196.27 |

-continued

| Line # | Billed | Paid | APC Wgt | RVU Wgt | Reprice Method | Discount Factor | Restated Total Weight | Allocated Billed | Upper CF Limit | Lower CF Limit | Actual CF | CF Edit Flag | Restated Units | RRV |
|---|---|---|---|---|---|---|---|---|---|---|---|---|---|---|
| 12 | 128.00 | 273.4 | 0 | 1.09 | Repriced RBRVS | 1 | 1.09 | 128.00 | 824.5 | 20.00 | 117.43 | NORMAL | 1.0 | 196.27 |
| 13 | 119.00 | 78.30 | 0 | 0.33 | Repriced RBRVS | 1 | 0.33 | 119.00 | 824.5 | 20.00 | 360.61 | NORMAL | 1.0 | 59.42 |
| 14 | 45.00 | 40.13 | 0 | 0.16 | Repriced RBRVS | 1 | 0.16 | 45.00 | 824.5 | 20.00 | 281.25 | NORMAL | 1.0 | 28.81 |
| 15 | 238.24 | 55.18 | 0 | 0.22 | Repriced RBRVS | 1 | 1.21 | 238.24 | 824.5 | 20.00 | 195.46 | CF EDIT UPPER | 5.5 | 219.48 |
| 16 | 87.70 | 30.10 | 0 | 0.12 | Repriced RBRVS | 1 | 0.12 | 87.70 | 824.5 | 20.00 | 730.83 | NORMAL | 1.0 | 21.61 |
| 17 | 1,185.9 | 543.0 | 4.75 | 8.18 | Repriced APC | 1 | 4.75 | 1,218.14 | 528.5 | 44.20 | 256.45 | NORMAL | 1.0 | 821.13 |
| 18 | 554.48 | 543.0 | 4.75 | 8.04 | Repriced APC | 1 | 4.75 | 586.67 | 528.5 | 44.20 | 123.51 | NORMAL | 1.0 | 821.13 |
| 19 | 416.50 | 247.0 | 2.66 | 1.58 | Repriced APC | 1 | 2.66 | 434.53 | 528.5 | 44.20 | 163.36 | NORMAL | 1.0 | 459.83 |
| 20 | 379.50 | 337.2 | 0.83 | 0.49 | Repriced APC | 1 | 2.49 | 396.37 | 528.5 | 44.20 | 159.19 | NORMAL | 3.0 | 430.45 |

Example 4

Professional and Scheduled Outpatient Cost Normalization

Example 4 illustrates the invention as described in connection with FIG. 5. Accordingly, execution of step 412 provides the following exemplary data obtained by extracting Professional outpatient data from the database:

| Admit Type | Encounter # | Line # | Facility | CPT CODE | MODIFIER | UNITS | BILLED | Paid |
|---|---|---|---|---|---|---|---|---|
| Professional | 1236421286 | 1 | Clinic A | 88307 | 26 | 1 | 165 | 156.75 |
| Professional | 1236421286 | 2 | Clinic A | 88331 | 26 | 1 | 200 | 190 |
| Professional | 1236421286 | 3 | Clinic A | 88332 | 26 | 1 | 89 | 84.55 |
| Professional | 1236421286 | 4 | Clinic A | 88332 | 26 | 16 | 1424 | 1352.8 |
| Professional | 1236421286 | 5 | Clinic A | 99254 | ~ | 1 | 300 | 285 |
| Professional | 1236421286 | 6 | Clinic A | 00160 | QK | 28 | 1287 | 1222.65 |
| Professional | 1236421286 | 7 | Clinic A | 00160 | QX | 28 | 1188 | 1128.6 |
| Professional | 1236421286 | 8 | Clinic A | 00400 | QK | 3 | 234 | 222.3 |
| Professional | 1236421286 | 9 | Clinic A | 00400 | QX | 3 | 216 | 205.2 |
| | | | | | | | 5,103.00 | 4,847.85 |

Next, the units are adjusted; an adjustment factor is created depending on the modifier as described in step 414:

| Admit Type | Encounter # | Line # | Facility | CPT Code | Modifier | UNITS | BILLED | Paid | Modifier Adj |
|---|---|---|---|---|---|---|---|---|---|
| Prof | 1236421286 | 1 | Clinic A | 88307 | 26 | 1 | 165 | 156.75 | 1.00 |
| Prof | 1236421286 | 2 | Clinic A | 88331 | 26 | 1 | 200 | 190 | 1.00 |
| Prof | 1236421286 | 3 | Clinic A | 88332 | 26 | 1 | 89 | 84.55 | 1.00 |
| Prof | 1236421286 | 4 | Clinic A | 88332 | 26 | 16 | 1424 | 1352.8 | 1.00 |
| Prof | 1236421286 | 5 | Clinic A | 99254 | ~ | 1 | 300 | 285 | 1.00 |
| Prof | 1236421286 | 6 | Clinic A | 00160 | QK | 28 | 1287 | 1222.65 | 1.00 |
| Prof | 1236421286 | 7 | Clinic A | 00160 | QX | 28 | 1188 | 1128.6 | 1.00 |
| Prof | 1236421286 | 8 | Clinic A | 00400 | QK | 3 | 234 | 222.3 | 1.00 |
| Prof | 1236421286 | 9 | Clinic A | 00400 | QX | 3 | 216 | 205.2 | 1.00 |
| | | | | | | | 5,103.00 | 4,847.85 | |

Then, according to step 416, Scheduled Outpatient data is extracted:

| Admit Type | Encounter # | Line # | Facility | CPT CODE | MODIFIER | UNITS | BILLED | Paid |
|---|---|---|---|---|---|---|---|---|
| Scheduled OP | 1417540667 | 1 | Hospital C | 80048 | ~ | 1 | 146 | 38.23 |
| Scheduled OP | 1417540667 | 2 | Hospital C | 80061 | ~ | 1 | 93.15 | 56.64 |
| Scheduled OP | 1417540667 | 3 | Hospital C | 83036 | ~ | 1 | 73 | 52.39 |
| Scheduled OP | 1417540667 | 4 | Hospital C | G0001 | ~ | 1 | 20 | 24.07 |

And, the modifier adjusted to a technical component (TC) if TC exists on the RVU table, according to steps 418 and 420:

| Encounter # | Line # | Facility | CPT CODE | MODIFIER | UNITS | BILLED | Paid | Adj Modifier |
|---|---|---|---|---|---|---|---|---|
| 1417540667 | 1 | Hospital C | 80048 | ~ | 1 | 146 | 38.23 | TC |
| 1417540667 | 2 | Hospital C | 80061 | ~ | 1 | 93.15 | 56.64 | TC |
| 1417540667 | 3 | Hospital C | 83036 | ~ | 1 | 73 | 52.39 | TC |
| 1417540667 | 4 | Hospital C | G0001 | ~ | 1 | 20 | 24.07 | |
| | | | | | | 332.15 | 171.33 | |

The next step is combining the Professional and Scheduled Outpatient data according to step 422:

| Admit Type | Encounter # | Line # | Facility | CPT Code | Modifier | Units | Billed | Paid | Modifier Adj |
|---|---|---|---|---|---|---|---|---|---|
| Professional | 1236421286 | 1 | Clinic A | 88307 | 26 | 1 | 165 | 156.75 | 1.00 |
| Professional | 1236421286 | 2 | Clinic A | 88331 | 26 | 1 | 200 | 190 | 1.00 |
| Professional | 1236421286 | 3 | Clinic A | 88332 | 26 | 1 | 89 | 84.55 | 1.00 |
| Professional | 1236421286 | 4 | Clinic A | 88332 | 26 | 16 | 1424 | 1352.8 | 1.00 |
| Professional | 1236421286 | 5 | Clinic A | 99254 | ~ | 1 | 300 | 285 | 1.00 |
| Professional | 1236421286 | 6 | Clinic A | 00160 | QK | 28 | 1287 | 1222.65 | 1.00 |
| Professional | 1236421286 | 7 | Clinic A | 00160 | QX | 28 | 1188 | 1128.6 | 1.00 |
| Professional | 1236421286 | 8 | Clinic A | 00400 | QK | 3 | 234 | 222.3 | 1.00 |
| Professional | 1236421286 | 9 | Clinic A | 00400 | QX | 3 | 216 | 205.2 | 1.00 |
| Scheduled OP | 1417540667 | 1 | Hospital C | 80048 | TC | 1 | 146 | 38.23 | 1.00 |
| Scheduled OP | 1417540667 | 2 | Hospital C | 80061 | TC | 1 | 93.15 | 56.64 | 1.00 |
| Scheduled OP | 1417540667 | 3 | Hospital C | 83036 | TC | 1 | 73 | 52.39 | 1.00 |
| Scheduled OP | 1417540667 | 4 | Hospital C | G0001 | ~ | 1 | 20 | 24.07 | 1.00 |
| | | | | | | | 5435.1 | 5019.18 | |

Next, steps 424, 426 and 428 may be executed to obtain the following data:

| Admit Type | Encounter # | Line # | Facility | Modifier | Unit | Billed | Paid | Modifier Adj | Upper Unit Edit | Unit Edit Flag | Place of Service |
|---|---|---|---|---|---|---|---|---|---|---|---|
| Prof | 1236421286 | 1 | Clinic A | 26 | 1 | 165 | 156.75 | 1.00 | 3.84 | Actual Units | FAC |
| Prof | 1236421286 | 2 | Clinic A | 26 | 1 | 200 | 190 | 1.00 | 4.15 | Actual Units | FAC |
| Prof | 1236421286 | 3 | Clinic A | 26 | 1 | 89 | 84.55 | 1.00 | 16.21 | Actual Units | FAC |
| Prof | 1236421286 | 4 | Clinic A | 26 | 16 | 1424 | 1352.8 | 1.00 | 16.21 | Actual Units | FAC |
| Prof | 1236421286 | 5 | Clinic A | ~ | 1 | 300 | 285 | 1.00 | 2.49 | Actual Units | FAC |
| Prof | 1236421286 | 6 | Clinic A | XX | 28 | 1287 | 1222.6 | 1.00 | 32.23 | Actual Units | FAC |
| Prof | 1236421286 | 7 | Clinic A | XX | 28 | 1188 | 1128.6 | 1.00 | 32.23 | Actual Units | FAC |

-continued

| Admit Type | Encounter # | Line # | Facility | Modifier | Unit | Billed | Paid | Modifier Adj | Upper Unit Edit | Unit Edit Flag | Place of Service |
|---|---|---|---|---|---|---|---|---|---|---|---|
| Prof | 1236421286 | 8 | Clinic A | XX | 3 | 234 | 222.3 | 1.00 | 15.39 | Actual Units | FAC |
| Prof | 1236421286 | 9 | Clinic A | XX | 3 | 216 | 205.2 | 1.00 | 15.39 | Actual Units | FAC |
| Sched OP | 1417540667 | 1 | Hospital C | TC | 1 | 146 | 38.23 | 1.00 | 2.85 | Actual Units | NON |
| Sched OP | 1417540667 | 2 | Hospital C | TC | 1 | 93.15 | 56.64 | 1.00 | 2.62 | Actual Units | NON |
| Sched OP | 1417540667 | 3 | Hospital C | TC | 1 | 73 | 52.39 | 1.00 | 2.94 | Actual Units | NON |
| Sched OP | 1417540667 | 4 | Hospital C | ~ | 1 | 20 | 24.07 | 1.00 | 2.55 | Actual Units | NON |

Then, a billed per weight may be created, the conversion factor may be applied and units may be edited and adjusted if applicable as described in steps 430, 432 and 433:

| Admit Type | Encounter # | Total Weight | Billed/ unit (CF) | Upper CF Edit | Lower CF Edit | CF Edit Flag | UNITS | Total Weight |
|---|---|---|---|---|---|---|---|---|
| Professional | 1236421286 | 2.31 | 71.43 | 312.29 | 24.12 | NORMAL | 1 | 2.31 |
| Professional | 1236421286 | 1.72 | 116.28 | 312.29 | 24.12 | NORMAL | 1 | 1.72 |
| Professional | 1236421286 | 0.86 | 103.49 | 312.29 | 24.12 | NORMAL | 1 | 0.86 |
| Professional | 1236421286 | 13.76 | 103.49 | 312.29 | 24.12 | NORMAL | 16 | 13.76 |
| Professional | 1236421286 | 3.67 | 81.74 | 312.29 | 24.12 | NORMAL | 1 | 3.67 |
| Professional | 1236421286 |  | 45.96 | 597.81 | — | NORMAL | 28 | 0 |
| Professional | 1236421286 |  | 42.43 | 597.81 | — | NORMAL | 28 | 0 |
| Professional | 1236421286 |  | 78.00 | 277.13 | — | NORMAL | 3 | 0 |
| Professional | 1236421286 |  | 72.00 | 277.13 | — | NORMAL | 3 | 0 |
| Scheduled OP | 1417540667 | 0.27 | 540.74 | 312.29 | 24.12 | CF EDIT UPPER | 6.57 | 1.77 |
| Scheduled OP | 1417540667 | 0.50 | 186.30 | 312.29 | 24.12 | NORMAL | 1 | 0.5 |
| Scheduled OP | 1417540667 | 0.37 | 197.30 | 312.29 | 24.12 | NORMAL | 1 | 0.37 |
| Scheduled OP | 1417540667 | 0.17 | 117.65 | 312.29 | 24.12 | NORMAL | 1 | 0.17 |

When these operations are complete, the overall rates for RRV may be created according to step 434 and as follows:

| Encounter Line Type | Billed | Total Weights | Overall Rate |
|---|---|---|---|
| RRV | 4,020,025,544 | 47,476,000 | 84.67 |

Then, according to step 436, the RRV may be created as follows:

| Admit Type | Encounter # | Total Wt | Billed/ Wt or Billed/ unit (CF) | Upper CF Edit | Lower CF Edit | CF Edit Flag | Restated Units | Restated Total Weight | HPRRV RATE | HPRRV |
|---|---|---|---|---|---|---|---|---|---|---|
| Prof | 1236421286 | 2.31 | 71.43 | 312.29 | 24.12 | NORMAL | 1.00 | 2.31 | 84.67 | 195.60 |
| Prof | 1236421286 | 1.72 | 116.28 | 312.29 | 24.12 | NORMAL | 1.00 | 1.72 | 84.67 | 145.64 |
| Prof | 1236421286 | 0.86 | 103.49 | 312.29 | 24.12 | NORMAL | 1.00 | 0.86 | 84.67 | 72.82 |
| Prof | 1236421286 | 13.76 | 103.49 | 312.29 | 24.12 | NORMAL | 16.00 | 13.76 | 84.67 | 1,165.13 |
| Prof | 1236421286 | 3.67 | 81.74 | 312.29 | 24.12 | NORMAL | 1.00 | 3.67 | 84.67 | 310.76 |

-continued

| Admit Type | Encounter # | Total Wt | Billed/ Wt or Billed/ unit (CF) | Upper CF Edit | Lower CF Edit | CF Edit Flag | Restated Units | Restated Total Weight | HPRRV RATE | HPRRV |
|---|---|---|---|---|---|---|---|---|---|---|
| Prof | 1236421286 | — | 45.96 | 597.81 | — | NORMAL | 28.00 | — | 52.5 | 1,470.00 |
| Prof | 1236421286 | — | 42.43 | 597.81 | — | NORMAL | 28.00 | — | 52.5 | 1,470.00 |
| Prof | 1236421286 | — | 78.00 | 277.13 | — | NORMAL | 3.00 | — | 51.45 | 154.35 |
| Prof | 1236421286 | — | 72.00 | 277.13 | — | NORMAL | 3.00 | — | 51.45 | 154.35 |
| Sched OP | 1417540667 | 0.27 | 540.74 | 312.29 | 24.12 | CF EDIT UPPER | 6.57 | 1.77 | 84.67 | 150.12 |
| Sched OP | 1417540667 | 0.50 | 186.30 | 312.29 | 24.12 | NORMAL | 1.00 | 0.50 | 84.67 | 42.34 |
| Sched OP | 1417540667 | 0.37 | 197.30 | 312.29 | 24.12 | NORMAL | 1.00 | 0.37 | 84.67 | 31.33 |
| Sched OP | 1417540667 | 0.17 | 117.65 | 312.29 | 24.12 | NORMAL | 1.00 | 0.17 | 84.67 | 14.39 |
| | | | | | | | | | | 5,376.82 |

Example 5
Pharmacy Cost Normalization

With reference to FIG. 6, exemplary data is provided to show cost normalization for pharmacy claims:

Thus, with reference to FIG. 6, initially according to step 512, the pharmacy data is extracted from the patient database as follows:

| Admit Type | Encounter # | Line # | Facility | NDC | DAYS | BILLED | Paid |
|---|---|---|---|---|---|---|---|
| Pharmacy | 12444002096 | 1 | Pharmacy A | 00093417774 | 10 | 56.7 | 46.7 |
| Pharmacy | 12444002108 | 1 | Pharmacy A | 62856024330 | 30 | 100.69 | 90.69 |
| | | | | | | 157.39 | 137.39 |

Then, according to steps 514, 516 and 518, the following restated day data is obtained:

| Admit Type | Encounter # | Line # | Facility | Days | Billed | Paid | Billed/ Day | Upper CF Edit | Lower CF Edit | CF Edit Flag | Re-Stated Days |
|---|---|---|---|---|---|---|---|---|---|---|---|
| Pharm | 12444002096 | 1 | Pharm A | 10 | 56.7 | 46.7 | 5.67 | 5.59 | 0.50 | CF EDIT UPPER | 22 |
| Pharm | 12444002108 | 1 | Pharm A | 30 | 100.69 | 90.69 | 3.36 | 12.33 | 0.91 | NORMAL | 30 |

Next, step 517 provides the median billed per unit by NDC code as follows:

| NDC | Rate/Day |
|---|---|
| 00093417774 | 2.535 |
| 62856024330 | 3.767 |

Ultimately, according to step 520, the RRV is created according to the formula:

RRV=Restated Days×Rate per Day:

| Admit Type | Line # | Facility | Days | Billed | Paid | Billed/ Day | Upper CF Edit | Lower CF Edit | CF Edit Flag | Re-Stated Days | HPRRV |
|---|---|---|---|---|---|---|---|---|---|---|---|
| Pharm | 1.00 | Pharm A | 10 | 56.70 | 46.70 | 5.67 | 5.59 | 0.50 | CF EDIT UPPER | 22.37 | 56.70 |

-continued

| Admit Type | Line # | Facility | Days | Billed | Paid | Billed/ Day | Upper CF Edit | Lower CF Edit | CF Edit Flag | Re-Stated Days | HPRRV |
|---|---|---|---|---|---|---|---|---|---|---|---|
| Pharm | 1.00 | Pharm A | 30 | 100.69 | 90.69 | 3.36 | 12.33 | 0.91 | Normal | 30.00 | 113.01 |
| | | | | 157.39 | 137.39 | | | | | | 169.71 |

The above specification describes certain preferred embodiments of this invention. This specification is in no way intended to limit the scope of the claims. Other modifications, alterations, or substitutions may now suggest themselves to those skilled in the art, all of which are within the spirit and scope of the present invention. It is therefore intended that the present invention be limited only by the scope of the attached claims below:

The invention claimed is:

1. A method for measuring and utilizing efficiency of resources utilized by health care providers in the care of medical conditions, comprising:
 providing a programmed digital computer for compiling a patient database comprising data from more than one component of care, wherein the component of care data further comprises data from at least one provider; and
 wherein the more than one component of care further comprises:
  acute inpatient;
  non-acute inpatient;
  hospital outpatient;
  professional and scheduled outpatient; and
  pharmacy;
 providing at least one component of care analysis module;
 wherein the at least one component of care analysis module further comprises:
  acute inpatient analysis module;
  non-acute inpatient analysis module;
  hospital outpatient analysis module;
  professional and scheduled outpatient analysis module; and
  pharmacy analysis module;
 wherein the acute inpatient analysis module further comprises:
  extracting acute inpatient data from the patient database;
  summing the extracted data to admission level;
  extracting DRG weights from the patient database;
  merging DRG weights with extracted inpatient data;
  identifying outliers, minimum volume data points and ungroupable DRGs;
  providing a programmed digital computer for creating a conversion factor using non-outlier and ungroupable data;
  providing a programmed digital computer for creating an RRV for outliers, non-outliers, minimum volume data points and ungroupable DRGs; and
  adjusting a modular RRV by allocating the modular RRV to an encounter level;
 wherein the non-acute inpatient analysis module further comprises:
  extracting non-acute inpatient data from the patient database;
  grouping extracted data into two admission groupings comprising hospital based and skilled nursing;
  summing extracted grouped data to admission level;
  calculating a billed per data rate per admission;
  identify outliers and create categories of identified outliers according to presence or absence of length of stay;
  identify non-outlier data and create categories of non-outlier data according to presence or absence of length of stay;
  creating median billed per day by admission grouping for outliers categorized as having length of stay;
  creating median billed per day by admission grouping for outliers categorized as having no length of stay;
  creating the modular RRV for each category of data; and
  adjusting the modular RRV by allocating the modular RRV to the encounter level;
 wherein the hospital outpatient analysis module further comprises:
  extracting hospital outpatient data from the patient database;
  excluding scheduled outpatient data from the patient database;
  creating unit limits on the extracted data;
  performing unit edit checks on the extracted data;
  summing the data to encounter line level;
  merging APC and RBRVS weights;
  creating total weight per line and billed amount per line;
  creating APC and RBRVS conversion factors;
  creating median billed per unit per procedure code for non-weighted procedures;
  identifying total weight errors based on line level conversion actor;
  performing unit edit and restating unit field;
  creating RRV for APC line;
  creating RRV for RBRVS line; and
  creating RRV for non-weighted procedures;
 wherein the professional and scheduled outpatient analysis module further comprises:
  extracting professional data from the patient database;
  applying RBRVS weight adjustment factor to the extracted professional data;
  extracting scheduled outpatient data from the patient database;
  identifying RBRVS procedure codes that break out technical component weight;
  identifying technical component procedure codes in extracted scheduled outpatient data;
  combining extracted scheduled outpatient and professional data and sum the combined data to encounter line level;
  identifying anesthesia encounter lines;
  merging on RBRVS weights by procedure code and modifier;
  creating total weight per line and billed amount per total weight;
  creating RBRVS conversion factor and median billed per unit for non-weighted procedure codes;
  editing and restating unit fields where appropriate;
  creating RRV for RBRVS line; and creating RRV for non-weighted procedures, including anesthesia;
wherein the pharmacy analysis module further comprises:
   extracting pharmacy data from the patient database;
   summing the extracted data to claim number level;
   creating a billed per day metric;
   performing day edits based on claim level billed per day; and
   creating a claim level RRV;
selecting at least one component of care to analyze;
extracting data corresponding to the at least one selected component of care from the patient database;
providing the extracted data to the appropriate component of care analysis module;
identifying and treating outliers from the data;
generating a modular Relative Resource Value (RRV) using the appropriate component of care analysis module;
providing a programmed digital computer for adjusting the modular RRV to allow inter-modular comparison by provider;
providing a programmed digital computer for compensating for preventive care and chronic care medical resources;
performing inter-modular comparison of the adjusted modular RRV by provider; and
ranking providers across all components of care based on the adjusted modular RRV.

2. The method of claim 1, further comprising:
providing at least one treatment plan option for patient treatment;
using the adjusted RRV to measure resource use for treatment plan options; and
comparing efficiency of provider resource use for the treatment plan options.

3. The method of claim 1, further comprising:
providing at least one treatment plan; and
measuring the resource use required for the treatment plan using the adjusted RRV.

4. The method of claim 1, further comprising using the RRV as an operational metric statistic for a health care provider.

5. The method of claim 1, further comprising:
providing a health care provider network, comprising more than one health care provider; and
using the RRV to assist in improving the efficiency and quality of the medical care delivered by health care provider network.

6. The method of claim 1, further comprising using the RRV to assist in improving the efficiency and quality of health care delivery.

7. The method of claim 6, further comprising using the RRV to assist in the identification of misuse of health care resources.

8. The method of claim 1, further comprising:
providing a plurality of treatment plans, each treatment plan comprising at least one treatment option for at least one medical condition, the treatment plans being provided by a plurality of health care providers; and
using the RRV to measure relative price for treatment plans across at east one medical condition and at least one provider.

9. The method of claim 1, further comprising using the RRV to evaluate the efficiency of collaborative treatment of patients by more than one provider.

10. The method of claim 1, further comprising using the RRV to evaluate and improve the efficient use of pharmaceutical resources.

11. The method of claim 1, further comprising:
providing at least one new treatment plan, comprising at least one treatment option; and
using the RRV to determine the relative efficiency of the at least one new treatment plan.

* * * * *